United States Patent
Bryant et al.

(10) Patent No.: US 6,787,526 B1
(45) Date of Patent: Sep. 7, 2004

(54) METHODS OF TREATING HEPATITIS DELTA VIRUS INFECTION WITH β-L-2′-DEOXY-NUCLEOSIDES

(75) Inventors: Martin L. Bryant, Carlisle, MA (US); Jean-Pierre Sommadossi, Birmingham, AL (US)

(73) Assignee: Idenix Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 10/329,616

(22) Filed: Dec. 26, 2002

Related U.S. Application Data

(63) Continuation of application No. 09/867,110, filed on May 29, 2001, now Pat. No. 6,596,700, and a continuation of application No. 09/863,816, filed on May 23, 2001.
(60) Provisional application No. 60/207,538, filed on May 26, 2000.

(51) Int. Cl.$^7$ .................... A01N 43/04; A61K 31/70; A61K 38/21
(52) U.S. Cl. .................... 514/45; 514/46; 514/47; 514/48; 514/49; 514/50; 514/894; 424/85.4
(58) Field of Search .................... 514/45, 46, 47, 514/48, 49, 50, 894

(56) References Cited

U.S. PATENT DOCUMENTS

| | | |
|---|---|---|
| 4,522,811 A | 6/1985 | Eppstein et al. |
| 4,619,896 A | 10/1986 | Shattock et al. |
| 4,916,122 A | 4/1990 | Chu et al. |
| 4,957,924 A | 9/1990 | Beauchamp |
| 5,149,794 A | 9/1992 | Yatvin et al. |
| 5,190,926 A | 3/1993 | Chu et al. |
| 5,194,654 A | 3/1993 | Hostetler et al. |
| 5,223,263 A | 6/1993 | Hostetler et al. |
| 5,256,641 A | 10/1993 | Yatvin et al. |
| 5,411,947 A | 5/1995 | Hostetler et al. |
| 5,416,203 A | 5/1995 | Letsinger |
| 5,463,092 A | 10/1995 | Hostetler et al. |
| 5,539,116 A | 7/1996 | Liotta et al. |
| 5,543,389 A | 8/1996 | Yatvin et al. |
| 5,543,390 A | 8/1996 | Yatvin et al. |
| 5,543,391 A | 8/1996 | Yatvin et al. |
| 5,554,728 A | 9/1996 | Basava et al. |
| 5,559,101 A | 9/1996 | Weis et al. |
| 5,565,438 A | 10/1996 | Chu et al. |
| 5,567,688 A | 10/1996 | Chu et al. |
| 5,587,362 A | 12/1996 | Chu et al. |
| 5,703,058 A | 12/1997 | Schinazi et al. |
| 5,747,044 A | 5/1998 | Houghton et al. |
| 5,750,350 A | 5/1998 | Houghton et al. |
| 5,770,584 A | 6/1998 | Kucera et al. |
| 5,932,219 A | 8/1999 | Houghton et al. |
| 5,939,402 A | 8/1999 | Weis et al. |
| 6,020,167 A | 2/2000 | Thoma |
| 6,025,335 A | 2/2000 | Weis et al. |
| 6,194,391 B1 | 2/2001 | Schinazi et al. |
| 6,245,749 B1 | 6/2001 | Schinazi et al. |
| 6,297,222 B1 | 10/2001 | von Borstel et al. |
| 6,395,716 B1 * | 5/2002 | Gosselin et al. ............... 514/45 |
| 6,444,652 B1 | 9/2002 | Gosselin et al. |
| 6,566,344 B1 | 5/2003 | Gosselin et al. |
| 6,569,837 B1 | 5/2003 | Gosselin et al. |
| 6,596,700 B2 * | 7/2003 | Sommadossi et al. ........ 514/45 |

FOREIGN PATENT DOCUMENTS

| | | |
|---|---|---|
| DE | 4224737 A1 | 2/1994 |
| EP | 0352248 A1 | 1/1990 |
| EP | 0350287 A2 A3 | 1/1990 |
| EP | 0355131 B1 | 2/1990 |
| EP | 0494119 A1 | 7/1992 |
| JP | 06293645 A | 10/1994 |
| WO | WO 89/02733 A1 | 4/1989 |
| WO | WO 89/03838 A1 | 5/1989 |
| WO | WO 90/00555 A1 | 1/1990 |
| WO | WO 91/16920 A1 | 11/1991 |
| WO | WO 91/18914 A1 | 12/1991 |
| WO | WO 91/19721 A1 | 12/1991 |
| WO | WO 92/08727 A1 | 5/1992 |
| WO | WO 92/15308 A1 | 9/1992 |
| WO | WO 92/18517 A1 | 10/1992 |
| WO | WO 93/00910 A1 | 1/1993 |
| WO | WO 94/01138 A1 | 1/1994 |
| WO | WO 94/20523 A1 | 9/1994 |
| WO | WO 94/26273 A1 | 11/1994 |
| WO | WO 94/29331 A1 | 12/1994 |
| WO | WO 95/07086 A1 | 3/1995 |
| WO | WO 95/07287 A1 | 3/1995 |
| WO | WO 95/20595 A1 | 8/1995 |
| WO | WO 95/32984 A1 | 12/1995 |
| WO | WO 96/11204 A1 | 4/1996 |
| WO | WO 96/13512 A1 | 5/1996 |
| WO | WO 96/15132 A2 | 5/1996 |
| WO | WO 96/29336 A1 | 9/1996 |
| WO | WO 96/40164 A1 | 12/1996 |
| WO | WO 97/31641 A1 | 9/1997 |
| WO | WO 98/15563 A1 | 4/1998 |
| WO | WO 00/09531 A2 A3 | 2/2001 |
| WO | WO 01/72294 A2 | 10/2001 |
| WO | WO 01/96353 A2 A3 | 12/2001 |

OTHER PUBLICATIONS

Arner, E.J., et al., "Mammalian Deoxyribonucleoside Kinases," *Pharm, Ther.*, 67(2):155–186 (1995).

Beauchamp, L.M., et al., "Amino Acid Ester Prodrugs of Acyclovir", *Antiviral. Chem. Chemother.*, 3(3):157–164 (1992).

Berk, A.J., et al., "A Genetically Distinct Tymidine Kinase in Mammalian Mitochondria," *J. Biol. Chem.*, 248:2722–2729, (1973).

(List continued on next page.)

*Primary Examiner*—James O. Wilson
*Assistant Examiner*—Traviss C. McIntosh, III
(74) *Attorney, Agent, or Firm*—Sherry M. Knowles, Esq.; King & Spalding LLP

(57) ABSTRACT

A method and composition for treating a host infected with hepatitis D comprising administering an effective hepatitis D treatment amount of a described 2′-deoxy-β-L-erythro-pentofuranonucleoside or a pharmaceutically acceptable salt or prodrug thereof.

25 Claims, 6 Drawing Sheets

OTHER PUBLICATIONS

Bestwick, R.K., et al., "Selective Expansion of Mitochondrial Nucleoside Triphosphate Pools in Antimetabolite-treated HeLa Cells," *J. Biol. Chem.*, 257:9300–9304 (1982).

Bhat, V., et al., "A Simple and Convenient Method for the Selective N-Acylations of Cytosine Nucleosides," *Nucleosides & Nucleotides*, 8(2): 179–183 (1989).

Bloch, et al., *J. Med. Chem.*, 10(5):908–12 (1967).

Boudou, V., et al., "A New and Convenient Approach for the Synthesis of Ribo–and 2'–Deoxyribo–β– L–Furanonucleosides Starting from β–L–Xylofuranonucleosides," *Nucleosides & Nucleotides* (Marcel Dekker), 18(4&5):607–609 (1999).

Bridges et al., "Characterization of a dCTP Transport Activity Reconstituted from Human Mitochondria," *J. Biol. Chem.*, 274(8):4620–4625 (Feb. 19, 1999).

Bridges, E.G., et al., "Identification of a Novel Mitochondrial dNTP Carrier and Its Interaction with Anti–HIV Nucleoside Analogs," *Proc. Am. Assoc. Cancer Res.*, 38:414 (Mar. 1997).

Bridges et al., "Inhibition of Mammalian DNA Polymerase–Associated 3' to 5' Exonuclease Activity by 5'–Monophosphates of 3'–Azido–3'–Deoxythymine and 3'–Amino–3'–Deoxythymidine," *Biochem. Pharm.*, 45(8):1571–1576 (1993).

Bryant et al., "Antiviral L–Nucleosides Specific for Hepatitis B Virus Infection," *Antimicrobial Agents and Chemotherapy*, 45(1):229–235 (Jan. 2001).

Casey, J.L. et al., *Antiviral Ther.*, 5(Suppl. 1), 32, Abstract 057 (2000).

Chang, C.N., et al., "Biochemical Pharmacology of (+)–and (–)–2',3'–Dideoxy–3'–thiacytidine as Anti–hepatitis B Virus Agents," *J. Biol. Chem.*, 267(31):22414–22420, (Nov. 5, 1992).

Chang, P., et al., "Deoxycytidine Deaminase–resistant Stereoisomer is the Active Form of (–)–2',3'–thiacytidine in the Inhibition of Hepatitis B Virus Replication," *J. Biol. Chem.*, 267(20):13938–13942 (Jul. 15, 1992).

Chariot et al., "Zidovudine–induced Mitochondrial Disorder with Massive Liver Streatosis Myopathy, Lactic Acidosis, and Mitochondrial DNA Depletion," *J. Hepatology*, 30:156–160 (1999).

Chen, M.S., et al., "Characterization of Pyrimidine Deoxyribonucleoside Kinase (Thymidine Kinase) and Thymidylate Kinase as a Multifunctional Enzyme in Cells Transformed by Herpes Simplex Virus Type 1 and in Cells Infected with Mutant Strains of Herpes Simplex Virus," *J. Virol.*, 30:942–945 (Jun. 1979).

Chen, C.–H., et al., "Delayed Cytotoxicity and Selective Loss of Mitochondrial DNA in Cells Treated with the Anti–human Immunodeficiency Virus Compound 2',3'–Dideoxycytidine," *J. Biol. Chem.*, 264:11934–11937 (1989).

Chen, C.–H., et al., "The Role of Cytoplasmic Deoxycytidine Kinase in the Mitochondrial Effects of the Anti–human Immunodeficiency Virus Compound 2',3'–Dideoxycytine," *J. Biol. Chem.*, 267(5):2856–2859 (Feb. 15, 1992).

Cote, P.J. et al., *Hepatology* 32(4Pt 1):807–817 (2000).

Cui, L., et al., "Effect of Nucleoside Analogs on Neurite Regeneration and Mitochondrial DNA Synthesis in PC–12 Cells," *Pharmacology & Experimental Therapeutics*, 280(3):1228–1234 (1997).

Davis, A.F., et al., "In Situ Localization of Mitochondrial DNA Replication in Intact Mammalian Cells," *J. Cell Biol.*, 135:883–893 (1996).

Davisson S.L., et al., *J. Org. Chem.*, 52(9):1794–1801 (1987).

Di Marco, V. et al., *J. Viral. Hepat.*, 3:123–8 (1996).

Doong et al., "Inhibition of the Replication of Hepatitis B Virus in Vitro by 2',3'–dideoxy–3'–thiacytidine and Related Analogues," *Proc. Natl. Acad. Sci.*, 88:8495–8499 (Oct. 1991).

Doong, S.L. et al., *Proc. Natl. Acad. Sci. U.S.A.*, 88:8495–9 (1991).

Du et al., Synthesis, "Anti–Human Immunodeficiency Virus and Anti–Hepatitis B Virus Activities of Novel Oxaselenolane Nucleosides," *J. Med. Chem.*, (40)19:2991–2993 (Sep. 12, 1997).

Dutschman, G.E., et al., "Metabolism of 2',3'–dideoxy–2', 3'–didehydro–β–L–(–)–5–Fluorocytidine and Its Activity in Combination with Clinically Approved Anti–Humna Immunodeficiency Virus β–D–(+) Nucleoside Analogs In Vitro," *Antimicrobial Agents & Chemotherapy*, 42(7):1799–1804 (Jul. 1998).

Farci, P. et al., *N. Engl. J. Med.*, 330:88–94 (1994).

Furman, et al., "The Anti–Hepatitis B Virus Activities, Cytotoxicities, and Anabolic Profiles of the (–) and (+) Enantiomers of cis–5–Fluoro–1–[2–(Hydroxymethyl)–1, 3–oxathiolane–5–yl]–Cytosine," *Antimicrobial Agents & Chemotherapy*, 36(12):2686–2692 (Dec. 1992).

Gaubert, G., et al., "Unnatural Enantiomers of 5–azacytidine Analogues: Synthesis and Enzymatic Properties," *Eur. J. Mol. Chem.*, 35:1011–1019 (2000).

Glonek, T., et al., "Full Anhydrization of Methylendiphosphonic Acid and of Phosphoric Acids by a Carbodiimide," *Inorg. Chem.*, 14(7):1597–1602(1975).

Gosselin, G., et al., "Anti–Human Immunodeficiency Virus Activities of the β–L Enantiomer of 2',3'–Dideoxycytidine and Its 5–Fluoro Derivative in Vitro," *Antimicrobial Agents & Chemotherapy*, 38(6):1292–1297 (1994).

Gosselin, G., et al., "Synthesis and Antiviral Evaluation of β–L–Xylofuranosyl Nucleosides of the Five Naturally Occurring Nucleic Acid Bases," *J. Heterocyclic Chem.*, 30:1229–1233 (1993).

Hadziyannis, S. J. *J. Hepatol.*, 13(Suppl 1):S2–6 (1991).

Hernandez–Santiago, B., et al., "Pharmacology of β–L–Thymidine and βL–2'–Deoxycytidine in HepG2 Cell and Primary Human Hepatocytes: Relavance to Chemotherapeutic Efficacy against Hepatitis B Virus," *Antimicrobial Agents & Chemotherapy*, 46(6):1728–1733 (Jun. 2002).

Hoard et al., *J. Am. Chem. Soc.*, 87(8): 1785–1788 (1965).

Holy, A., "Nucleic Acid Components and Their Analogs. CLIII. Preparation of 2'–deoxy–L–Ribonucleosides of the Pyrimidine Series," *Collect.Czech.Chem.Commun.*, 37(12):4072–87 (1972).

Honkoop, P., et al., "Lamivudine Treatement in Patients with Chronic Hepatitis Delta Infection," *Hepatology*, 24(Supp.):1219 (Abstract) (1997).

Hoofnagle, J. et al., *Prog. Clin. Biol. Res.*, 234:291–8 (1987).

Hostetler, K.Y., et al. "Greatly Enhanced Inhibition of Human Immunodeficiency Virus Type 1 Replication In CEM and HT4–6C Cells By 3'–Deoxythymidine Diphosphate Dimyristoylglycerol, A Lipid Prodrug Of 3'–Deoxythymidine," *Antimicrob. Agents Chemother.*, 36:2025–2029 (Sep. 1992).

Hostetler, K.Y., et al., "Synthesis and Antiretroviral Activity of Phospholipid Analogs of Azidothymidine and Other Antiviral Nucleosides," *J. Biol. Chem.*, 265(11):6112–7 (Apr. 15, 1990).

Imai et al., *J. Org. Chem.*, 34(6):1547–1550 (1969).

Iwai, I., et al., "Synthetic Procedures in Nucleic Acid Chemistry," W. W. Aorbach and R.S. Tipson, eds., John Wiley & Sons, Inc. New York, 1:135–138 (1968).

Jones, R. et al., "Mini Review: Nucleotide prodrugs," *Antiviral Research*, 27:1–17 (1995).

Jurovĉik, M., and Holy, A., "Metabolism of pyrimidine L–nucleosides," *Nucleic Acids Research*, 3(8):2143–2153 (Aug. 1976).

Korba et al., "A Cell Culture Assay for Compounds Which Inhibit Hepatitis B Virus Replication," *Antiviral Res.*, 15:217 (1991).

Korba, B.E. et al., *Hepatology*, 31(5):1165–1175 (2000).

Krayevsky, A.A., and Chernov, P.N., "Can a Substrate Enantiomer Be a Substrate for the Same Enzyme?, " *Mol. Biol.*, 30(5):585–591 (1996).

Krayevsky, A.A. and Chernov, P.N. "Should the Assymetric of Enzymatic Active Centers Always Correlate with the Asymmetry of their Substrates?," *J. Biomolecular Structure & Dynamics*, 14(2):225–230 (1996).

Kucera, L.S., et al., "Novel membrane–interactive Ether Lipid Analogs That Inhibit Infectious HIV–1 Production and Induce Defective Virus Formation," *AIDS Res Hum Retroviruses*, 6:491–501 (May 1990).

Labenz, J., et al., "Analysis of the TK Enzyme Complex Induced by HSV Types 1 and 2 by Means of Isoelectric Focusing and Polyacyrlamide Gel Electrophoresis," *Arch. Virol.*, 71:235–249 (1982).

Lau, D.T., et al., "Lamivudine for Chronic Delta Hepatitis," *Hepatology*, 30(2):546–549 (1999).

Lin, T.–S. et al., "Design and Synthesis of 2',3'–Dideoxy–2'3'–didyhydro–α–L–Fd4C), Two Exceptionally Potent Inhibitors of Human HBV and Potent Inhibitors of HIV In Vitro," *J. Med. Chem.*, 39(9):1757–1759 (Apr. 26,1996).

Lin, T.S., et al., "Synthesis and Antiviral Activity of Various 3–40 –azido Analogues of Pyrimidine Deoxyribonucleosides Against Human Immunodeficiency Virus (HIV–1, HTLV–III/LAV)," I *J. Med. Chem.*, 31(2):336–340 (1988).

Lin et al., "Synthesis and Biological Evaluation of 2',3'–Dideoxy–L–pyrimidine Nucleosides as Potential Antiviral Agents against HIV and HBV," *J. Med. Chem.*, 97:98–803 (1994).

Lin et al., "Synthesis of Several Pyrimidine L–Nucleoside Analogues as Potential Antiviral Agents," *Tetrahedron Letters*, vol. 51(4):1055–1068 (1995).

Maga et al., "Lack of Stereospecificity of Suid Pseudorabies Virus Thymidine Kinase," *Biochem. J.*, 294(2):381–385 (Sep. 1, 1993).

Mahmoudian, "Quantitative Structure–Activity Relationships (QSARs) of Pyrimidine Nucleosides as HIV–1 Antivival Agents," *Pharm. Research*, 8(1):43–46 (1991).

Mansour et al., "Stereochemical Aspects of the Anti–HCMV Activity of Cytidine Nucleoside Analogues," *Antiviral Chemistry & Chemotherapy*, 6(3):138–142 (1994).

Marchand, A., et al, "Stereospecific Synthesis of Unnatural β–L–enantiomers of 2–Chloroadenine Pentofuranonucleoside Derivatives," *J. Chem. Soc. Perkin Trans. 1*, 1999(16):2249–2254 (1999).

Nakayama, C., et al., "Synthetic Nucleosides and Nucleotides. XX. Synthesis of Various 1–β–Xylofuranosyl–5–Alkyluracils and Related Nucleosides," *Nucleosides & Nucleotides*, 1:139–146 (1982).

Ness, R.K. in *Synthetic Procedures in Nucleic Acid Chemistry*, Zorbach, W.W., Tipson, R.S., Eds.; J. Wiley and Sons; New York, Vol 1:83:187 (1968).

Niro, G.A., et al., "The Predominance of Hepatitis Delta Virus Genotype 1 Among Chronically Infected Italian Patients," *Hepatology*, 25(3):728–734 (1997).

Norbeck, *Tetrahedron Letters*, 30 (46):6246 (1989).

Pan–Zhou, X–R., et al., "Differential Effects of Antiretroviral Nucleoside Analogs on Mitochondrial Function in HepG2 Cells," *Antimicrobial Agents & Chemotherapy*, 44(3):496–503 (Mar. 2000).

Pankiewicz, et al., "Synthesis of Methylenebis(phosphonate) Analogs of ADP Ribose," *Collect. Czech. Chem. Commun.*, 61:S92–S95 (Sep. 23, 1996).

Pankiewicz, et al., "Efficient Synthesis of Methylenebis (phosphonate) Analogues of P1,P2–disubstituted Pyrophosphates of Biological Interest. A Novel Plausible Mechanism.," *J. Am. Chem. Soc.*, 119:3691–3695 (Apr. 15, 1997).

Placidi et al., "Cellular Pharmacology of βL–thymidine and β–L–2'–deoxycytidine in HepG2 cells and Primary Rat, Monkey and Human Hepatocytes," $3^{rd}$ Int. Conf. Ther. Vir. Hepatitis, abstr. A122, [Antivir. Ther. 4, Suppl. 4] (1999).

Porres, J.C. et al., *J. Hepatol.*, 9:338–344 (1989).

Recondo, E.F., and Rinderknecht, H. "Eine neue, Einfache Synthese des 1–O–Acetyl–2,3, 5–Tri–O–βD–Ribofuranosides," *Helv. Chim. Acta.*, 1171–1173 (1959).

Robins, "Selective Deoxygenation and Modification at C2'of Nucleosides," *Nucleic Acids Research Symposium Series*, vol. 11: Pp. 1–4, Kyoto, Japan, Nov. 24–26, 1982, A.E. Pritchard (ed.), IRL Press, Ltd., Oxford, England, (1982).

Robins, M.J., et al., "Nucleic Acid Related Compounds. 42. A General Procedure for the Efficient Deoxygenation of Secondary Alcohols. Regiospecific and Stereoselective Conversion of Ribonucleosides to 2'–Deoxynucleosides," *J. Am. Chem. Soc.*, 105:4059–4065 (1983).

Rosina, F. et al., *Hepatology*, 13:1052–6 (1991).

Rosina, F. et al., *Prog. Clin. Biol. Res.*, 234:299–303 (1987).

Ryu, E.K., et al., "Aminoacyl Derivatives of Nucleosides, Nucleotides, and Polynucleotides. XXVII. General Synthesis of 2'(3')–O–aminoacyl Dinucleoside Phosphates Derived From the AA–tRNA Terminus," *Journal of Carbohydrates–Nucleosides–Nucleotides* (Marcel Dekker), 4(6):387–408 (1977). XP000564974.

Saneyoshi, M., and Satoh, E. "Synthetic Nucleosides and Nucleotides. XIII. Stannic Chloride Catalyzed Ribosylation of Several 6–Substituted Purines," *Chem. Pharm. Bull.*, 27:2518–2521 (1979).

Schinazi, et al., "Advances in Therapies for Viral Hepatitis," *Antiviral Therapy*, 3(3):vii–ix (1998).

Schinazi, et al., "Selective Inhibition of Human Immunodefiency Viruses by Racemates and Enantiomers of cis–5–Fluoro–1–[2–(Hydroxymethyl)–1, 3–Oxathiolane–5–yl] Cytosine," *Antimicrobial Agents and Chemotherapy*, 36(11):2423–2431 (1992).

Schinazi, et al., "Effect of Combinations of Acylovir with Vidarabine or its 'Monophosphate on Herpes Simplex Viruses in Cell Culture and in Mice," *Antimicrobial Agents and Chemotherapy*, 22(3):499, (1982).

Shuto, S., et al., "A Facile One–step Synthesis of 5'–Phosphatidylnucleosides by an Enzymatic Two–Phase Reaction," *Tetrahedron Letters*, 28:199–202 (1987).

Skaric, V., et al., "Aminoacyl Derivatives of 4–Thiothymidine, Cytosine and Cytidine," *Croatica Chemica Acta*, 48(3):351–359 (1976). XP001034973.

Smedile, A. et al., *Prog Liver Dis.*, 12:157–75 (1994).

Söderlund and Arner, "Mitochondrial versus Cytosololic Activities of Deoxyribonucleoside Salvage Enzymes," *Purine and Pyrimidine Metabolism in Man VIII*, A.Shota & M. Taylor (ed.), Plenum Press, New York, 201–204 (1995).

Spadari et al., "L–Thymidine is Phosphorylated by Herpes Simplex Type 1 Thymidine Kinase and Inhibits Viral Growth," *J. Med. Chem.*, 35(22):4214–4220 (1992).

Sureau, et al., "Production of Infectious Hepatitis Delta Virus In Vitro and Neutralization with Antibodies Directed against Hepatitis B Virus Pre–S Antigens," *Journal of Virology*, 1241–1245 (1992).

Thomas, H.C. et al., *Prog. Clin. Biol. Res.*, 234:277–90 (1987).

Tsai, C.–H., et al., "Effect of Anti–HIV 2'–B–Fluoro–2', 3'–Dideoxynucleoside Analogs on the Cellular Content of Mitochondrial DNA and on Lactate Production," *Biochem, Pharmacol.*, 48(7): 1477–1481 (1994).

Tyrsted et al., "Inhibition of the Synthesis of 50–Phosphoribosyl–1–Pyrophosphate by 3'–Deoxy–Adenosine and Structurally Related Nucleoside Analogs," *Biochem, Biophys. Acta*, 155(2):619–22 (Feb. 26, 1968).

Verri et al., "Relaxed Enantioselectivity of Human Mitochondrial Thymidine Kinase and Chemotherapeutic Uses of L–Nucleoside Analogs," *Biochem J.*, 328(1):317–20 (Nov. 15, 1997).

Verri et al., "Lack of Enantiospecificity of Human–2'–Deoxycytidine Kinase:Relevance for the Activation of Beta–L–Deoxycytidine Analogs as Antineoplastic and Antiviral Agents," *Mol. Pharmacol*, 51(1):132–138 (Jan. 1997).

von Janta–Lipinski et al., "Newly Synthesized L–Enantiomers of 3'Fluoro–Modified β–2'–Deoxyribonucleoside 5'–Triphosphates Inhibit Hepatitis B DNA Polymerase but not the Five Cellular DNA Polymerases, α,β, δ, and βNor HIV–1 Reverse Transcriptase," *J. Medicinal Chemistry*, 41(12):2040–2046 (Jun. 4, 1998).

Wang, P. et al., "Recent Advances in L–Nucleosides: Chemistry and biology," *Antiviral Research* (Elsevier), 40(1/2):19–44 (1998). XP000944025.

Wang, S., et al., "Activity of Nucleoside and Non–Nucleoside Reverse Transcriptase Inhibitors (NNRTI) Against Equine Infectious Anemia Virus (EIAV)," *First National Conference on Human Retroviruses and Related Infectious*, Washington, D.C., (Dec. 12–16, 1993).

Wang et al., *Hepatology*, 24 (Suppl):1219 (1997).

Zedeck, M.S., et al., "Pseudomonas Testosteroni", *Mol. Phys.*, 3(4):386–95 (1967).

Zhang, W., et al., "Removal of Silyl Protecting Groups from Hydroxyl Functions with Ammonium Fluoride in Methanol," *Tetrahedron Lett.*, 33:1177–1180 (1992).

Zhu, Y.L., et al., "Anti–Hepatitis B Virus Activity and Metabolism of 2',3'–dideoxy–2', 3'–didehydro–β–L–(–)–5–Fluorocytidine," *Antimicrobial Agents & Chemotherapy*, 42(7):1805–1810 (Jul. 1998).

Zhu, C., et al., "Incorporation of Nucleoside Analogs into Nuclear or Mitochondrial DNA Is Determined by the Intracellular Phosphorylation Site, " *J. Biol. Chem.*, 275(35):26727–26731 (2000).

Zhu, Y.L., et al., "Inhibition of Replication of Hepatitis B Virus by Cytallene In Vitro," *Antimicrobial Agents & Chemotherapy*, 41(8):1755–1760 (Aug. 1997).

* cited by examiner

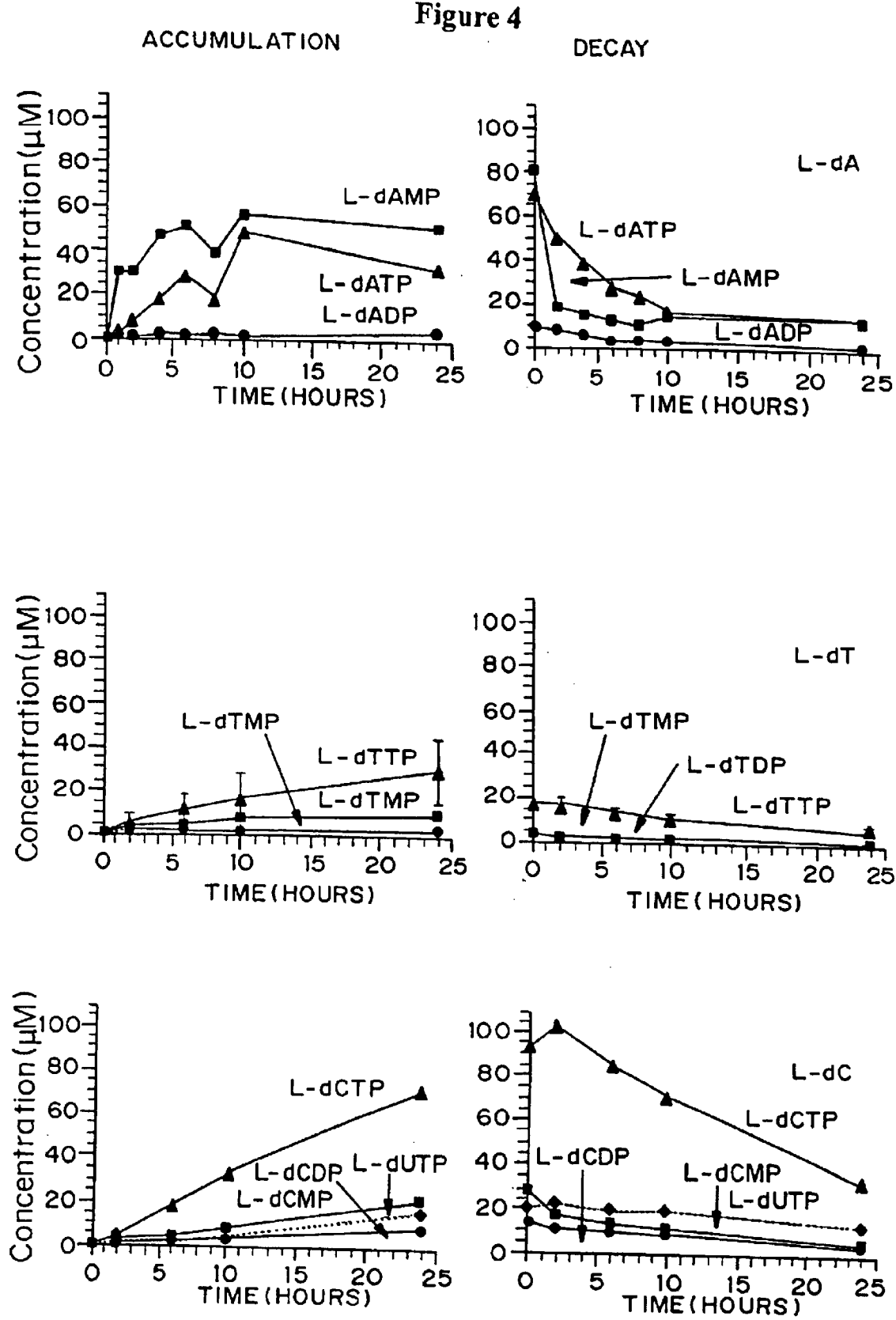

Antiviral Effect of βL-dA, βL-dt and βL-dC in Woodchuck Chronic Hepatitis Model
(n=3 per drug treatment group, n=4 per placebo group, dose 10 mg/kg orally once per day)

METHODS OF TREATING HEPATITIS DELTA VIRUS INFECTION WITH β-L-2'-DEOXY-NUCLEOSIDES

If a continuing application, continuation of prior application Ser. No. 09/863,816 filed May 23, 2001 and is a continuation of Ser. No. 09/867,110 filed May 29, 2001 now U.S. Pat. No. 6,596,700.

This application claims priority to U.S. provisional application No. 60/207,538, filed on May 26, 2000.

FIELD OF THE INVENTION

This invention is in the area of methods and compositions for the treatment of a host infected with hepatitis delta virus (also referred to as "HDV") that includes administering an effective amount of a defined β-L-2'-deoxy-nucleoside or a pharmaceutically acceptable salt or prodrug thereof.

BACKGROUND OF THE INVENTION

Type D hepatitis, the most severe form of viral hepatitis, is caused by infection with hepatitis D (delta) virus (HDV), a sub-viral satellite of hepatitis B virus (HBV) (Smedile, A. et al. *Prog Liver Dis* 1994, 12, 157–75). Compared with other agents of viral hepatitis, acute HDV infection is more often associated with fulminant hepatitis, a rapidly progressive, often fatal form of the disease in which massive amounts of the liver are destroyed. Chronic type D hepatitis is typically characterized by necroinflammatory lesions, similar to chronic HBV infection, but is more severe, and frequently progresses rapidly to cirrhosis and liver failure, accounting for the disproportionate association of chronic HDV infection with terminal liver disease (Smedile, A. et al. *Prog Liver Dis* 1994, 12, 157–75; Rizzetto, M. et al. *Ann Intern Med* 1983, 98, 437–41). Although HDV infection affects fewer individuals than HBV alone, the resulting acute or chronic liver failure is a common indication for liver transplantation in Europe as well as North America (Smedile, A. and Rizzetto, M. *Int J Clin Lab Res* 1992, 22, 211–215; Wright, T. L. and Pereira, B. *Liver Transplant Surgery* 1995, 1, 30–42). Chronic disease affects 15 million persons worldwide, about 70,000 of whom are in the U.S. The Center for Disease Control estimates 1,000 deaths annually in the U.S. due to HDV infection (Alter, M. J. and Hadler, S. C. *Prog Clin Biol Res* 1993, 382, 243–50; Alter, M. J. and Mast, E. E. *Gastroenterol Clin North Am* 1994, 23, 437–55).

There is currently no generally accepted effective therapy for type D hepatitis, and liver transplantation is the only option for the associated end-stage liver disease. Although interferon alpha has been moderately successful in treating some cases of type D hepatitis, the need for better treatment options is indicated by the very high doses required, variable responses, frequent relapse after cessation of treatment, and difficulties in drug administration (Thomas, H. C. et al. *Prog Clin Biol Res* 1987, 234, 277–90; Hoofnagle, J. et al. *Prog Clin Biol Res* 1987, 234, 291–8; Rosina, F. et al. *Prog Clin Biol Res* 1987, 234, 299–303; Rosina, F. et al. *Hepatology* 1991, 13, 1052–6; Farci, P. et al. *N Engl J Med* 1994, 330, 88–94; Hadziyannis, S. J. *J Hepatol* 1991, 13(Suppl 1), S21–6; Di Marco, V. et al. *J Viral Hepat* 1996, 3, 123–8; Porres, J. C. et al. *J Hepatol* 1989, 9, 338–44).

The HDV virion is composed of a ribonucleoprotein core and an envelope. The core contains HDV-RNA, and hepatitis delta antigen (HDAg), which is the only protein encoded by this virus (Wang, K. S. et al. *Nature* 1986, 323, 508–14). The envelope is formed by the surface antigen protein (hepatitis B surface antigen, or HBsAg) of the helper virus, hepatitis B (Bonino, F. *Infect Immun* 1984, 43, 1000–5; Bonino, F. et al. *Hepatology* 1981, 1, 127–31; Bonino, F. et al. *J Virol* 1986, 58, 945–50). The envelope is the sole helper function provided by HBV. HDV is able to replicate its RNA within cells in the absence of HBV (Kuo, M. Y. et al. *J Virol* 1989, 63, 1945–50), but requires HBsAg for packaging and release of HDV virions (Wu, J. C. et al. *J Virol* 1991, 65, 1099–104; Ryu, W. S. et al. *J Virol* 1992, 66, 2310–2315), as well as for infectivity (Sureau, C., et al. *J Virol* 1992, 66, 1241–5). As a result of the dependence of HDV on HBV, HDV infects individuals only in association with HBV.

Lamivudine (β-L-2',3'-dideoxy-3'-thiacytidine, 3TC) is a synthetic nucleoside shown to be effective in treating HIV and HBV infection. See U.S. Pat. No. 5,539,116 to Liotta et al. Lamivudine is known to cause sustained suppression of HBV replication during treatment (Nevens, F. et al. *Gastroenterology* 1997, 113, 1258–1263). However, lamivudine does not improve disease activity or lower HDV-RNA levels in patients with chronic delta hepatitis (Lau, D. T. et al. *Hepatology* 1999, 30, 546–9). Lamivudine was recently approved in the U.S. and several other countries for treatment of chronic HBV infection. Prolonged treatment of chronic HBV carriers with lamivudine leads to decreased levels of HBV in serum and improved liver histology (Lai, C. L. et al. *N Engl J Med* 1998, 339, 61–8; Tyrrell, D. et al. *Hepatology* 1993, 18, 112A; Nevens, F. et al. *Gastroenterology* 1997, 113, 1258–63; Dienstag, J. L. et al. *N Engl J Med* 1995, 333, 1657–61). Despite the dramatic effects on HBV, lamivudine treatment of patients chronically infected with both HBV and HDV has little effect on circulating levels of HDV; more importantly, there is no improvement in disease activity even though HBV levels are suppressed (Honkoop, P. et al. *Hepatology* 1997, 24(Suppl), 1219 (Abstract); Lau, D. T. et al. *Hepatology* 1999, 30, 546–9).

Additional forms of treatment have been tried. For example, suramin in vitro blocks the entry of the virion into hepatocytes, but it is too toxic to be acceptable for long term use in humans (Smedile, A. et al. *Prog Liver Dis* 1994, 12, 157–75). Acyclovir enhances HDV replication in vitro (Smedile, A. et al. *Prog Liver Dis* 1994, 12, 157–75). Ribavirin did not significantly affect virological or biochemical parameters and had severe side-effects (Smedile, A. et al. *Prog Liver Dis* 1994, 12, 157–75). Synthetic analogs of thymosin have also been ineffective in the treatment of HDV infection (Smedile, A. et al. *Prog Liver Dis* 1994, 12, 157–75).

None of the described treatments for HDV infection are generally accepted as effective.

Because the woodchuck hepatitis virus (WHV) is closely related to HBV (ca. 85% nucleic acid homology), it has been widely used as a model for HBV infection and disease in its natural host, the eastern woodchuck (*M. monax*) (Gerin, J. L. *Gastroenterol Jpn* 1990, 25 Supp, 38–42; Tennant, B. C. et al. *Viral Hepatitis and Liver Disease* 1988, 462–464). Experimentally infected woodchucks have also been used extensively for analysis and development of anti-HBV therapeutics (Zahm, F. E. et al. *Ital J Gastroenterol Hepatol* 1998, 30, 510–6; Tennant, B. C. et al. *Hepatology* 1998, 28, 179–91; Mason, W. S. et al. *Virology* 1998, 245, 18–32; Korba, B. E. et al. *Hepatology* 1996, 23, 958–63; Hurwitz, S. et al. *Antimicrob Agents Chemother* 1998, 42, 2804–2809; Block, T. M. et al. *Nat Med* 1998, 4, 610–4; Cullen, J. M. et al. *Antimicrob Agents Chemother* 1997, 41, 2076–82; Fourel, G. et al. *Nature* 1990, 347, 294–8; Gangemi, J. et al. *Antivir Therap* 1997, 1, 64–70; Genovesi, E. V. et al.

Antimicrob Agents Chemother 1998, 42, 3209–17; Korba, B. E. et al. *Antiviral Res* 2000, 45, 19–32; Cote, P. J. et al. *Hepatolopy* 2000, 31, 190–200; Korba, B. E. et al. *Antiviral Therapy* 2000, 5(2), 95–104; Korba, B. E. et al. *Antimicrobial Agents and Chemotherapy* 2000, 44(6), 1757–60; Korba, B. E. et al. *Antimicrobial Agents and Chemotherapy* 2000, 44(7), 1964–1969). The efficacy of several anti-HBV agents used to experimentally treat chronic WHV infection in woodchucks (araAMP, ribavirin, AZT, ACV, 3TC, famciclovir, FTC) has accurately paralleled the efficacy of these agents administered to HBV patients treated in the course of clinical trials. The similar efficacy observed in WHV infected woodchucks and HBV infected persons treated with anti-HBV agents demonstrates that the woodchuck animal model can be predictive for anti-HBV therapies in man (Zahm, F. E. et al. *Ital J Gastroenterol Hepatol* 1998, 30, 510–6; Tennant, B. C. et al. *Hepatology* 1998, 28, 179–91; Mason, W. S. et al. *Virology* 1998, 245, 18–32; Hurwitz, S. J. et al. *Antimicrob Agents Chemother* 1998, 42(11), 2804–2809; Fourel, G. et al. *Nature* 1990, 347, 294–8; Gangemi, J. et al. *Antivir Therap* 1997, 1, 64–70; Genovesi, E. V. et al. *Antimicrob Agents Chemother* 1998, 42, 3209–17; Korba, B. E. et al. *Antiviral Res* 2000, 45(1), 19–32; Korba, B. E. et al. *Hepatology* 2000, 32(4 Pt 1), 807–817; Korba, B. E. et al. *Hepatology* 2000, 31(5), 1165–1175; Korba, B. E. et al. *Antiviral Therapy* 2000, 5(2), 95–104). Like HBV, WHV can support HDV particle formation and infection, and the eastern woodchuck has been a useful model for HDV infection (Negro, F. et al. *J Virol* 1989, 63, 1612–8; Parana, R., Gerard, F., Lesbordes, J. L., Pichoud, C., Vitvitski, L., Lyra, L. G. & Trepo, C. *J Hepatol* 1995, 22, 468–73; Ciccaglione, A. R. et al. *Arch Virol* 1993, Suppl 8, 15–21; Bergmann, K. F. et al. *J Immunol* 1989, 143, 3714–21; Ponzetto, A. et al. *Proc Natl Acad Sci USA* 1984, 81, 2208–12; Ponzetto, A. et al. *Prog Clin Biol Res* 1987, 234, 37–46).

The dependence of HDV on its helper virus, HBV, could suggest that successful treatment of HDV infection would follow successful treatment of the supporting HBV infection, although, this does not appear to be the case, as illustrated by recent results obtained with the drug lamivudine (Glaxo-Wellcome, Inc.) (Honkoop, P. et al. *Hepatology* 1997, 24(Suppl), 1219 (Abstract); Lau, D. T. et al. *Hepatology* 1999, 30, 546–9). The lack of an effect of lamivudine on disease in HBV-HDV infected patients underscores the direct role of HDV in disease severity in such patients. Although lamivudine inhibits HBV and WHV replication, it does not affect the production of viral surface antigen (Lau, D. T. et al. *Hepatology* 1999, 30, 546–9; Doong, S. L. et al. *Proc Natl Acad Sci USA* 1991, 88, 8495–9; Korba, B. E. et al. *Hepatology* 2000, 32(4 Pt 1), 807–817; Korba, B. E. et al. *Hepatology* 2000, 31(5), 1165–1175). The life cycle of HBV and other representatives of this family of viruses (for example, WHV) is unique in that the process of replicating genomic copies of the virus and the production of viral proteins (for example, HBV or WHV surface antigens) are differentially regulated (Ganem, D. Hepadnaviridae In "Fields Virology", Fields B N, Knipe D M, Howley P, ed. Lippincott-Raven 1996 Philadelphia, 2703–2737). Therefore, antiviral agents, such as synthetic nucleosides (for example, lamivudine) which target viral polymerases, may significantly inhibit HBV replication (for example, as measured by a reduction in viremia), but not affect the level of viral mRNA or viral protein production (for example, as measured by the levels of HBV surface antigen in plasma or serum). Because formation of the viral envelope by the surface antigen protein is the only HBV and WHV function important for HDV, the failure to inhibit HBsAg production might play a role in the failure of lamivudine to affect HDV replication and disease.

U.S. Pat. No. 5,747,044 discloses recombinantly produced immunogenic HDV polypeptides useful as vaccines.

U.S. Pat. No. 5,932,219 to Chiron discloses the entire genome of the hepatitis D virus, a family of cDNA replicas of the entire HDV genome, and teaches that portions of these cDNA sequences are useful as probes to diagnose the presence of virus in clinical samples. The patent also discloses proteins encoded by the cDNA that are useful in the production of vaccines. In particular, the '219 patent discloses a vaccine for hepatitis D which incorporates the p24 and p27 viral polypeptides. U.S. Pat. No. 5,750,350 to Chiron claims a kit useful in the analysis of hepatitis D virus which includes a peptide encoded by ORF 5 of the HDV genome. U.S. Pat. No. 5,747,044 claims a recombinantly produced immunogenic particle which raises antibodies against HDV, wherein the particle includes an immunogenic polypeptide encoded within ORF 5 of the HDV nucleotide sequence or its complement.

U.S. Pat. No. 6,020,167 assigned to Medeva Holdings B. V. discloses a method for treating chronic hepatitis, and in particular, hepatitis B, that includes administering a composition containing HBsAg.

U.S. Pat. No. 5,770,584 discloses a method for treating hepatitis virus infection by administering alkyl lipids or alkyl lipid derivatives.

U.S. Pat. No. 4,619,896 discloses a process for unmasking delta antigen in the blood of an animal, that includes treating serum with a surfactant and optionally with an antibody-antigen dissociating agent. The blood derived delta antigen is used as a diagnostic agent in the detection and determination of different classes of antibodies to hepatitis D virus.

United States statutory invention registration H1,345 discloses a method for preventing or treating hepatitis virus by administering a protein-prenyl transferase inhibitor.

Sureau, et al. "Production of Infectious Hepatitis Delta Virus In Vitro and Neutralization with Antibodies Directed against Hepatitis B Virus Pre-S Antigens" *Journal of Virology* 1992, 1241–1245 discloses that HDV particles produced in vitro are infectious and that (i) infectious particles are coated with HBV envelope proteins that contain the pre-S1 and pre-S2 regions, (ii) epitopes of the pre-S1 and pre-S2 domains of HBV envelope proteins are exposed at the surface of HDV particles, and (iii) that antibodies directed against those epitopes have neutralizing activity against HDV.

Recently, it has been reported that L-FMAU is a potent inhibitor of HDV in chronically infected animals. (Casey, J. L. et al., *Antiviral Therapy* 2000, 5(Suppl. 1), 32, Abstract 057).

The synthetic nucleosides β-L-2'-deoxycytidine (β-L-2'-dC), β-L-2'-deoxythymidine (β-L-dT) and β-L-2'-deoxyadenosine (β-L-2'-dA), are also known in the art. Antonin Holy first disclosed β-L-dC and β-L-dT in 1972, "Nucleic Acid Components and Their Analogs. CLIII. Preparation of 2'-deoxy-L-Ribonucleosides of the Pyrimidine Series" *Collect Czech Chem Commun* 1972, 37(12), 4072–87. Morris S. Zedeck et al. first disclosed β-L-dA for the inhibition of the synthesis of induced enzymes in *Pseudomonas testosteroni* (*Mol Phys* 1967, 3(4), 386–95).

Certain 2'-deoxy-β-L-erythro-pentofuranonucleosides are known to have anti-neoplastic and selected antiviral activities. Verri et al. disclose the use of 2'-deoxy-β-L-erythropentofuranonucleosides as antineoplastic agents and as antiherpetic agents (*Mol Pharmacol* 1997, 51(1), 132–138 and *Biochem J* 1997, 328(1), 317–20). Saneyoshi et al. demonstrate the use of 2'-deoxy-L-ribonucleosides as reverse transcriptase (I) inhibitors for the control of retroviruses and for the treatment of AIDS, Japanese Kokai Tokyo Koho JP 06293645 (1994).

Giovanni et al. tested 2'-deoxy-β-L-erythropentofuranonucleosides against partially pseudorabies virus (PRV) (*Biochem J* 1993, 294(2), 381–5).

Chemotherapeutic uses of 2'-deoxy-β-L-erythropentofuranonucleosides were studied by Tyrsted et al. *Biochem Biophys Acta* 1968, 155(2), 619–22 and Bloch, et al. *J Med Chem* 1967, 10(5), 908–12.

β-L-2'-deoxythymidine (β-L-dT) is known in the art to inhibit herpes simplex virus type 1 (HSV-1) thymidine kinase (TK). Iotti et al., WO 92/08727, teaches that β-L-dT selectively inhibits the phosphorylation of D-thymidine by HSV-1 TK, but not by human TK. Spaldari et al. reported that L-thymidine is phosphorylated by herpes simplex virus type 1 thymidine kinase and inhibits viral growth, *J Med Chem* 1992, 35(22), 4214–20.

The synthetic nucleosides β-L-2'-deoxycytidine (β-L-2'-dC), β-L-2'-deoxythymidine (β-L-dT), β-L-2'-deoxyinosine (β-L-dI) and β-L-2'-deoxyadenosine (β-L-2'-dA) have recently been disclosed in the art for the treatment of hepatitis B virus. Gilles Gosselin et al. disclosed the use of β-L-dT, β-L-dA, β-L-dC and β-L-dI, and pharmaceutically acceptable salts and prodrugs thereof for the treatment of hepatitis B virus in WO 00/09531 (PCT/US99/18149).

PCT/US01/09987 filed by Georgetown University, Cornell University and the University of Georgia Research Foundation, Inc. describes that the administration of a nucleoside or nucleoside analog that substantially reduces the level of hepatitis B surface antigen (referred to therein as HBsAg) in a host is useful in the treatment of hepatitis delta viral infection in that host. In one embodiment PCT/US01/09987 describes that 2'-fluoro-5-methyl-beta-L-arabinofuranosyluridine (L-FMAU) significantly reduces the level of hepatitis B surface-antigen, and thus is useful in the treatment of hepatitis delta infections.

Because of the large number of persons infected with hepatitis delta virus, the devastating effects of hepatitis delta virus infection on the individual, and the lack of effective treatments, there is a critical need for new and effective for the treatment of hepatitis delta virus infection.

Therefore, it is an object of the present invention to provide methods for the treatment of a host, including a human, infected with hepatitis delta virus.

SUMMARY OF THE INVENTION

A method for the treatment of hepatitis delta infection in humans and other hosts is disclosed that includes administering an effective amount of a biologically active 2'-deoxy-β-L-erythro-pentofuranonucleoside (referred to alternatively herein as a β-L-d-nucleoside or a β-L-2'-d-nucleoside) or a pharmaceutically acceptable salt or prodrug thereof, administered either alone or in combination or alternation, optionally in a pharmaceutically acceptable carrier. The term 2'-deoxy, as used in this specification, refers to a nucleoside that has no substituent in the 2'-position.

The disclosed 2'-deoxy-β-L-erythropentofuranonucleosides, or pharmaceutically acceptable prodrugs or salts or pharmaceutically acceptable formulations containing these compounds are useful in the prevention and treatment of hepatitis D infections and other related conditions such as chronic liver inflammation caused by HDV, cirrhosis, acute hepatitis, fulminant hepatitis, chronic persistent hepatitis, and fatigue. These compounds or formulations can also be used prophylactically to prevent or retard the progression of clinical illness in individuals who are infected with HDV or who have been exposed to HDV.

In one embodiment of the present invention, the 2'-deoxy-β-L-erythro-pentofuranonucleoside derivative is a compound of the formula:

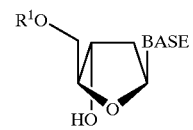

wherein $R^1$ is selected from the group consisting of H, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and BASE is a purine or pyrimidine base that may optionally be substituted.

In another embodiment of the present invention, the 2'-deoxy-β-L-erythro-pentofuranonucleoside derivative is β-L-2'-deoxypurine or a pharmaceutically acceptable salt or prodrug thereof, of the formula:

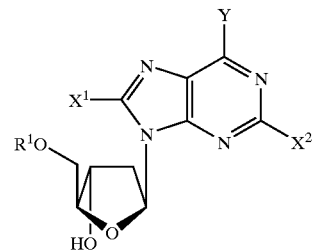

wherein $R^1$ is selected from the group consisting of H; straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

Y is $OR^3$, $NR^3R^4$ or $SR^3$; and $X^1$ and $X^2$ are independently selected from the group consisting of H, straight chained, branched or cyclic alkyl, CO-alkyl, CO-aryl, CO-alkoxyalkyl, halogen, $OR^5$, $NR^5NR^6$ or $SR^5$; and $R^3$, $R^4$, $R^5$ and $R^6$ are independently H, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In a particular embodiment, the 2'-deoxy-β-L-erythropentofuranonucleoside derivative is β-L-2'-deoxyadenosine or a pharmaceutically acceptable salt or prodrug thereof, of the formula:

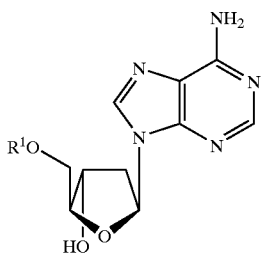

wherein R¹ is H, mono, di or tri phosphate, acyl, alkyl, or a stabilized phosphate derivative (to form a stabilized nucleotide prodrug).

In a preferred embodiment, R¹ is H.

In another particular embodiment, the 2'-deoxy-β-L-erythro-pentofuranonucleoside derivative is β-L-2'-deoxyguanosine or pharmaceutically acceptable salt or prodrug thereof of the formula:

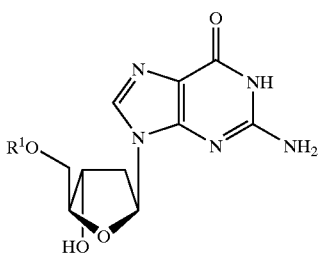

wherein R¹ is H, mono, di or tri phosphate, acyl, alkyl, or a stabilized phosphate derivative (to form a stabilized nucleotide prodrug).

In another particular embodiment, the 2'-deoxy-β-L-erythro-pentofuranonucleoside derivative is β-L-2'-deoxyinosine or pharmaceutically acceptable salt or prodrug thereof of the formula:

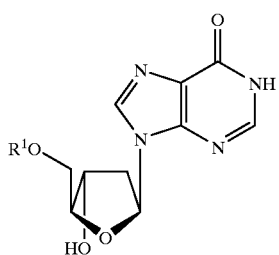

wherein R¹ is H, mono, di or tri phosphate, acyl, alkyl, or a stabilized phosphate derivative (to form a stabilized nucleotide prodrug).

In another embodiment of the present invention, the 2'-deoxy-β-L-erythro-pentofuranonucleoside derivative is β-L-2'-deoxypyrimidine or a pharmaceutically acceptable salt or prodrug thereof, of the formula:

wherein R¹ is selected from the group consisting of H, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

Y is $OR^3$, $NR^3R^4$ or $SR^3$; and

X¹ is selected from the group consisting of H, straight chained, branched or cyclic alkyl, CO-alkyl, CO-aryl, CO-alkoxyalkyl, halogen, $OR^5$, $NR^5NR^6$ or $SR^5$; and $R^3$, $R^4$, $R^5$ and $R^6$ are independently H, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In one particular embodiment, the 2'-deoxy-β-L-erythro-pentofuranonucleoside derivative is β-L-2'-deoxycytidine or pharmaceutically acceptable salt or prodrug thereof of the formula:

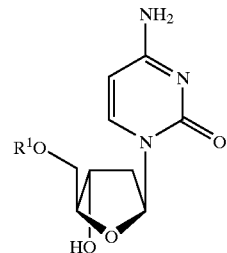

wherein R¹ is H, mono, di or tri phosphate, acyl, alkyl, or a stabilized phosphate derivative (to form a stabilized nucleotide prodrug).

In a preferred embodiment, R¹ is H.

In another embodiment, the 2'-deoxy-β-L-erythro-pentofuranonucleoside derivative is β-L-2'-deoxyuridine or pharmaceutically acceptable salt or prodrug thereof of the formula:

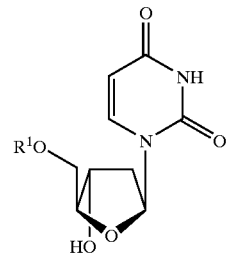

wherein R¹ is H, mono, di or tri phosphate, acyl, alkyl, or a stabilized phosphate derivative (to form a stabilized nucleotide prodrug).

In another embodiment, the 2'-deoxy-β-L-erythro-pentofuranonucleoside derivative is β-L-thymidine or a pharmaceutically acceptable salt or prodrug thereof of the formula:

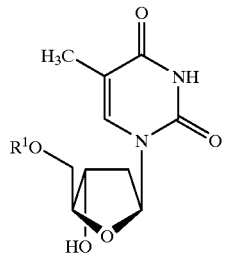

wherein R¹ is H, mono, di or tri phosphate, acyl, alkyl, or a stabilized phosphate derivative (to form a stabilized nucleotide prodrug).

In a preferred embodiment, R¹ is H.

In another embodiment, the 2'-deoxy-β-L-erythro-pentofuranonucleoside, its pharmaceutically acceptable salt or prodrug thereof, is administered in alternation or combination with one or more other 2'-deoxy-β-L-erythro-pentofuranonucleosides, its pharmaceutically acceptable salt or prodrug thereof, or one or more other compounds which exhibit activity against hepatitis D virus. In general, during alternation therapy, an effective dosage of each agent is administered serially, whereas in combination therapy, an effective dosage of two or more agents is administered together. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

In another embodiment, the invention includes a method for the treatment of humans infected with HDV that includes administering an HDV treatment amount of a prodrug of the disclosed 2'-deoxy-β-L-erythro-pentofuranonucleoside derivatives. A prodrug, as used herein, refers to a compound that is converted into the nucleoside on administration in vivo. Nonlimiting examples include pharmaceutically acceptable salt (alternatively referred to as "physiologically acceptable salts"), the 5', N⁴ (cytidine) and/or N⁶ (adenosine) acylated or alkylated derivatives of the active compound, the 5'-phospholipid, and/or the 5'-ether lipids of the active compound.

In a preferred embodiment, the 2'-deoxy-β-L-erythro-pentofuranonucleoside is in the form of a pharmaceutically acceptable prodrug, in that the 5'-hydroxyl is acylated with an amino acid. In an even more preferred embodiment, the amino acid is valine.

BRIEF DESCRIPTION OF THE FIGURES

FIG. 4 is a graph that illustrates the metabolism of L-dA, L-dC and L-dT in human HepG2 cells in terms of accumulation and decay. The cells were incubated with 10 μM of compound.

DETAILED DESCRIPTION OF THE INVENTION

Figure 1:
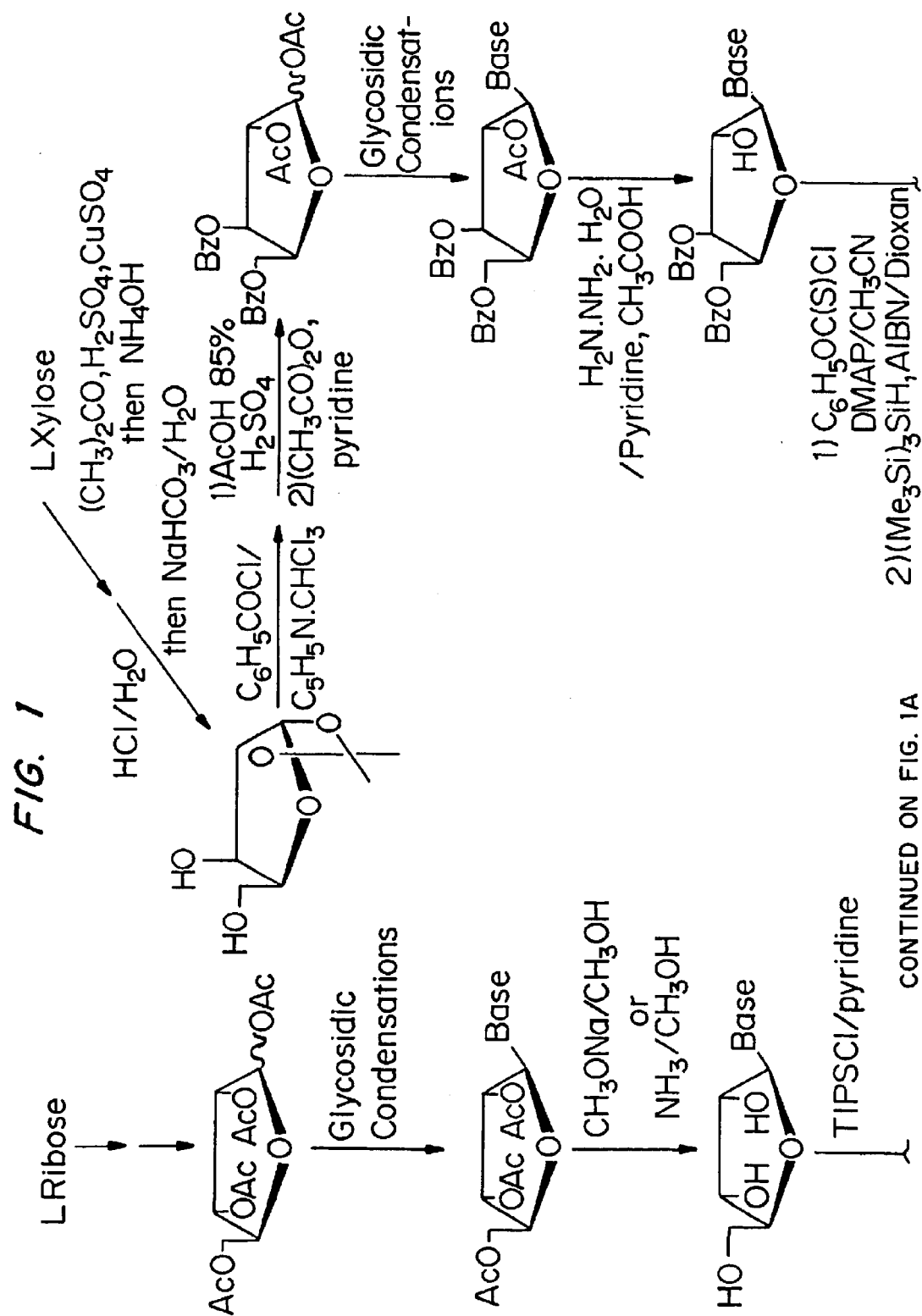
FIG. 1 illustrates a general process for obtaining β-L-erythro-pentafuranonucleosides (β-L-dN) using L-ribose or L-xylose as a starting material.
Figure 1A:
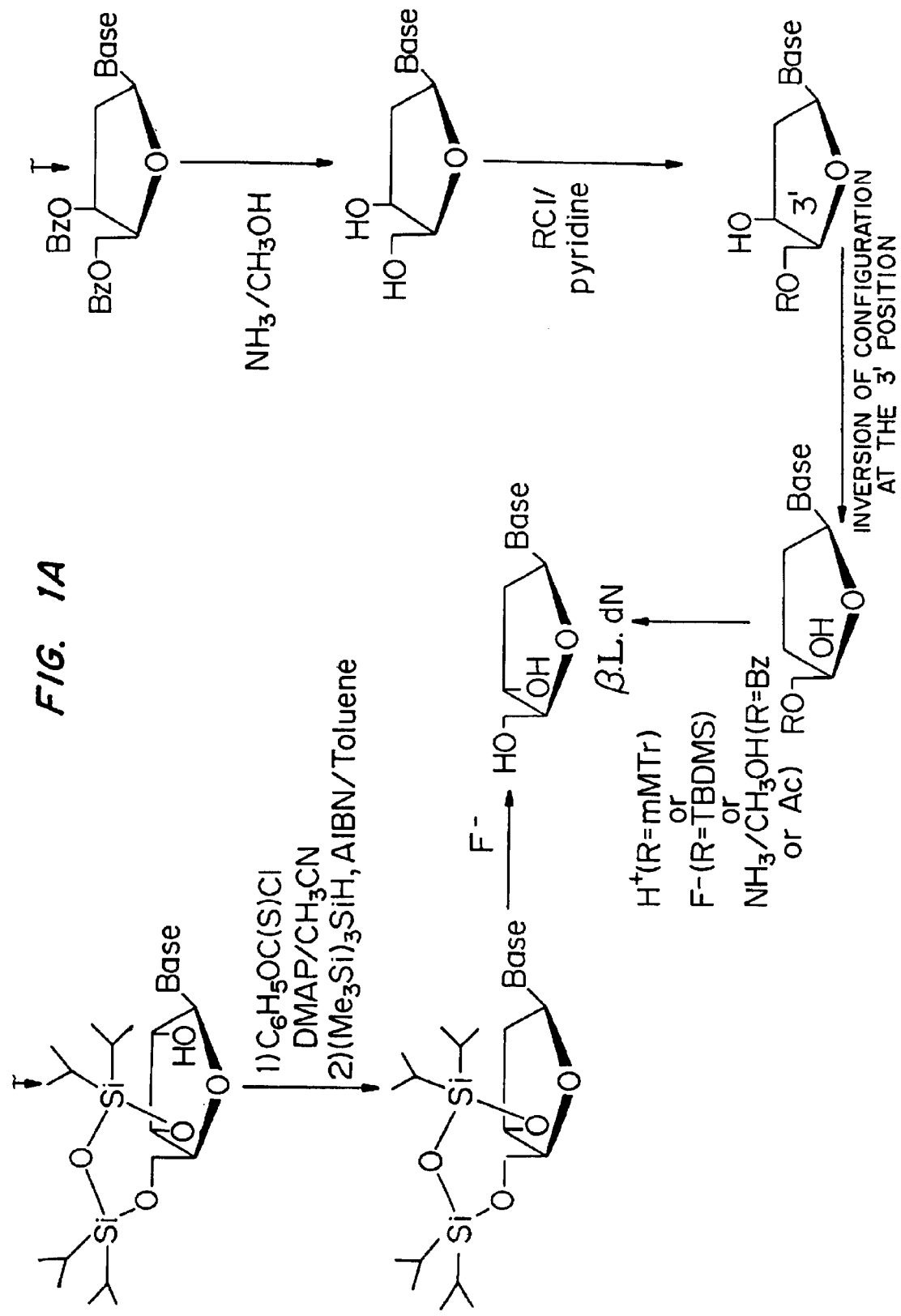
Figure 2:
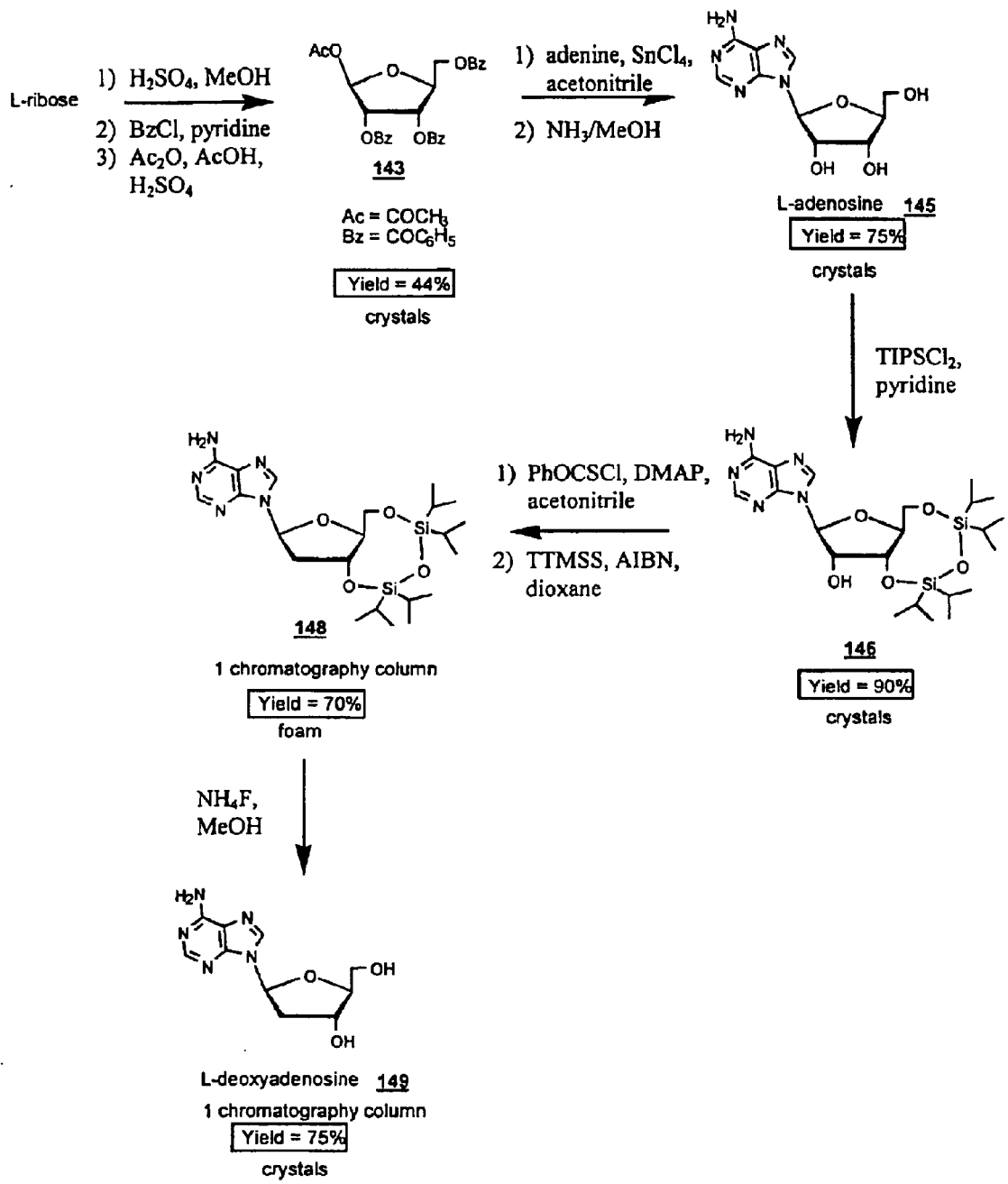
FIG. 2 illustrates a non-limiting example of the synthesis of L-deoxyadenosine using L-ribose as a starting material.
Figure 3A:
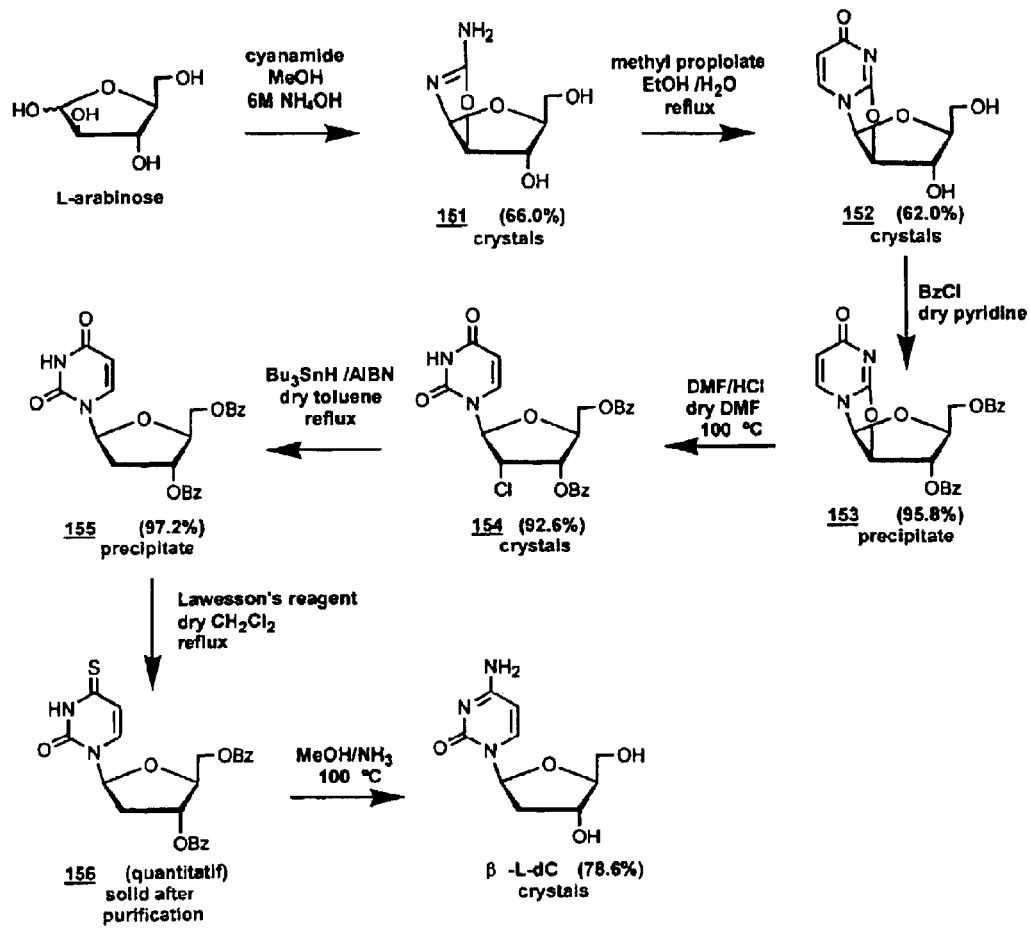
FIG. 3 illustrates a non-limiting example of the synthesis of β-L-dC (3a) and β-L-dT (3b) using L-arabinose as a starting material.
Figure 3B:
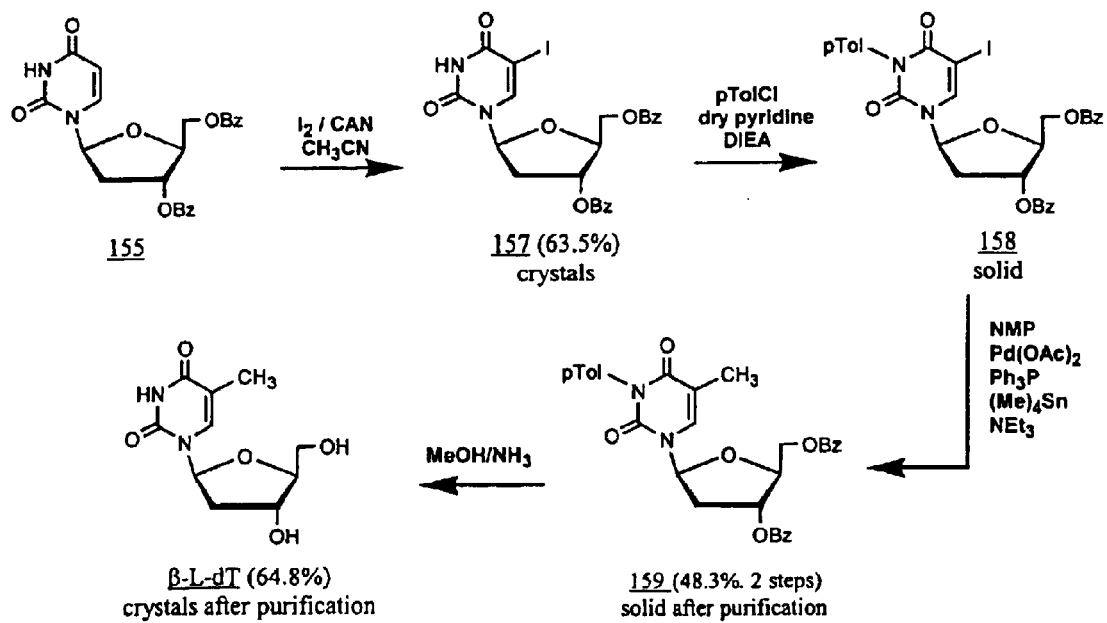

A method for the treatment of hepatitis delta infection in humans and other hosts is disclosed that includes administering an effective amount of a biologically active 2'-deoxy-β-L-erythro-pentofuranonucleoside (referred to alternatively herein as a β-L-d-nucleoside or a β-L-2'-d-nucleoside) or a pharmaceutically acceptable salt or prodrug thereof, administered either alone or in combination, optionally in a pharmaceutically acceptable carrier. The term 2'-deoxy, as used in this specification, refers to a nucleoside that has no substituent in the 2'-position.

The disclosed 2'-deoxy-β-L-erythro-pentofuranonucleosides, or pharmaceutically acceptable prodrugs or salts or pharmaceutically acceptable formulations containing these compounds are useful in the prevention and treatment of hepatitis D infections and other related conditions such as chronic liver inflammation caused by HDV, cirrhosis, acute hepatitis, fulminant hepatitis, chronic persistent hepatitis and fatigue. These compounds or formulations can also be used prophylactically to prevent or retard the progression of clinical illness in individuals who are infected with HDV or who have been exposed to HDV.

In one embodiment of the present invention, the 2'-deoxy-β-L-erythro-pentofuranonucleoside derivative is a compound of the formula:

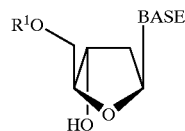

wherein R¹ is selected from the group consisting of H, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and BASE is a purine or pyrimidine base that may optionally be substituted.

In another embodiment of the present invention, the 2'-deoxy-β-L-erythro-pentofuranonucleoside derivative is β-L-2'-deoxypurine or a pharmaceutically acceptable salt or prodrug thereof, of the formula:

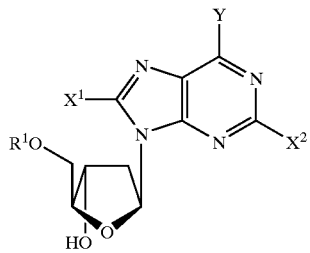

wherein R¹ is selected from the group consisting of H, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

Y is OR³, NR³R⁴ or SR³; and

X¹ and X² are independently selected from the group consisting of H, straight chained, branched or cyclic alkyl, CO-alkyl, CO-aryl, CO-alkoxyalkyl, halogen, OR⁵, NR⁵NR⁶ or SR⁵; and R³, R⁴, R⁵ and R⁶ are independently H, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In a particular embodiment, the 2'-deoxy-β-L-erythro-pentofuranonucleoside derivative is β-L-2'-deoxyadenosine or a pharmaceutically acceptable salt or prodrug thereof, of the formula:

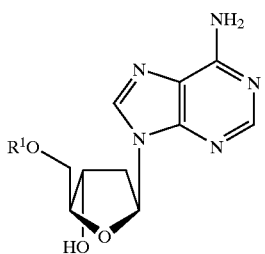

wherein R¹ is H, mono, di or tri phosphate, acyl, alkyl, or a stabilized phosphate derivative (to form a stabilized nucleotide prodrug).

In a preferred embodiment, R¹ is H.

In another particular embodiment, the 2'-deoxy-β-L-erythro-pentofuranonucleoside derivative is β-L-2'-deoxyguanosine or pharmaceutically acceptable salt or prodrug thereof of the formula:

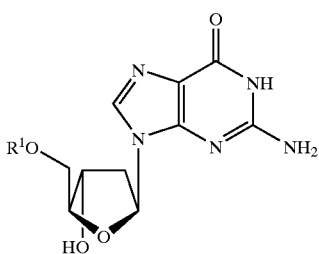

wherein R¹ is H, mono, di or tri phosphate, acyl, alkyl, or a stabilized phosphate derivative (to form a stabilized nucleotide prodrug).

In another particular embodiment, the 2'-deoxy-β-L-erythro-pentofuranonucleoside derivative is β-L-2'-deoxyinosine or pharmaceutically acceptable salt or prodrug thereof of the formula:

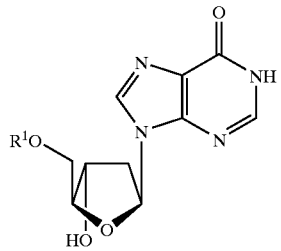

wherein R¹ is H, mono, di or tri phosphate, acyl, alkyl, or a stabilized phosphate derivative (to form a stabilized nucleotide prodrug).

In another embodiment of the present invention, the 2'-deoxy-β-L-erythro-pentofuranonucleoside derivative is β-L-2'-deoxypyrimidine or a pharmaceutically acceptable salt or prodrug thereof, of the formula:

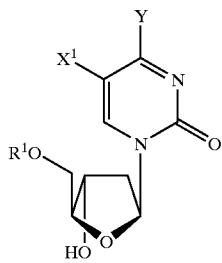

wherein R¹ is selected from the group consisting of H, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

Y is OR³, NR³R⁴ or SR³; and

X¹ is selected from the group consisting of H, straight chained, branched or cyclic alkyl, CO-alkyl, CO-aryl, CO-alkoxyalkyl, halogen, OR⁵, NR⁵NR⁶ or SR⁵; and R³, R⁴, R⁵ and R⁶ are independently H, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In one particular embodiment, the 2'-deoxy-β-L-erythro-pentofuranonucleoside derivative is β-L-2'-deoxycytidine or pharmaceutically acceptable salt or prodrug thereof of the formula:

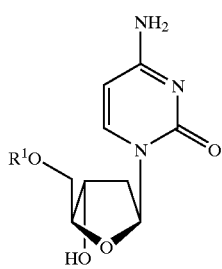

wherein R¹ is H, mono, di or tri phosphate, acyl, alkyl, or a stabilized phosphate derivative (to form a stabilized nucleotide prodrug).

In a preferred embodiment, $R^1$ is H.

In another embodiment, the 2'-deoxy-β-L-erythro-pentofuranonucleoside derivative is β-L-2'-deoxyuridine or pharmaceutically acceptable salt or prodrug thereof of the formula:

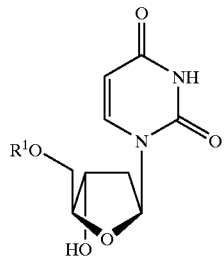

wherein $R^1$ is H, mono, di or tri phosphate, acyl, alkyl, or a stabilized phosphate derivative (to form a stabilized nucleotide prodrug).

In another embodiment, the 2'-deoxy-β-L-erythro-pentofuranonucleoside derivative is β-L-thymidine or a pharmaceutically acceptable salt or prodrug thereof of the formula:

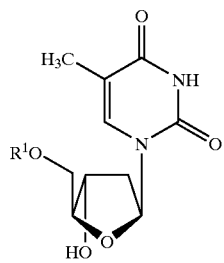

wherein $R^1$ is H, mono, di or tri phosphate, acyl, alkyl, or a stabilized phosphate derivative (to form a stabilized nucleotide prodrug).

In a preferred embodiment, $R^1$ is H.

In another embodiment, the 2'-deoxy-β-L-erythro-pentofuranonucleoside, its pharmaceutically acceptable salt or prodrug thereof, is administered in alternation or combination with one or more other 2'-deoxy-β-L-erythro-pentofuranonucleosides, its pharmaceutically acceptable salt or prodrug thereof, or one or more other compounds which exhibit activity against hepatitis D virus. In general, during alternation therapy, an effective dosage of each agent is administered serially, whereas in combination therapy, an effective dosage of two or more agents is administered together. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

In another embodiment, the invention includes a method for the treatment of humans infected with HDV that includes administering an HDV treatment amount of a prodrug of the disclosed 2'-deoxy-β-L-erythro-pentofuranonucleoside derivatives. A prodrug, as used herein, refers to a compound that is converted into the nucleoside on administration in vivo. Nonlimiting examples include pharmaceutically acceptable salt (alternatively referred to as "physiologically acceptable salts"), the 5', $N^4$ (cytidine) and/or $N^6$ (adenosine) acylated or alkylated derivatives of the active compound, the 5'-phospholipid, and/or the 5'-ether lipids of the active compound.

In a preferred embodiment, the 2'-deoxy-β-L-erythro-pentofuranonucleoside of the present invention is in the form of a pharmaceutically acceptable prodrug, in that the 5'-hydroxyl is acylated with an amino acid. In an even more preferred embodiment, the amino acid is valine.

Stereochemistry

As shown below, a nucleoside contains at least two critical chiral carbon atoms (*). In general, the substituents on the chiral carbons [the specified purine or pyrimidine base (referred to as the C1 substituent when using the sugar ring intermediate numbering) and $CH_2OH$ (referred to as the C4 substituent)] of the nucleoside can be either cis (on the same side) or trans (on opposite sides) with respect to the sugar ring system. Both the cis and trans racemates consist of a pair of optical isomers. Hence, each compound has four individual stereoisomers. The four stereoisomers are represented by the following configurations (when orienting the sugar moiety in a horizontal plane such that the —O— moiety is in back): (1) cis, with both groups "up", which is referred to as β-D; (2) the mirror image, i.e., cis, with both groups "down", which is the mirror image is referred to as β-L; (3) trans with the C4 substituent "up" and the C1 substituent "down" (referred to as α-D); and (4) trans with the C4 substituent "down" and the C1 substituent "up" (referred to as α-L). The two cis enantiomers together are referred to as a racemic mixture of β-enantiomers, and the two trans enantiomers are referred to as a racemic mixture of α-enantiomers.

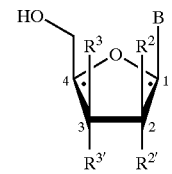

The four possible stereoisomers of the claimed compounds are illustrated below.

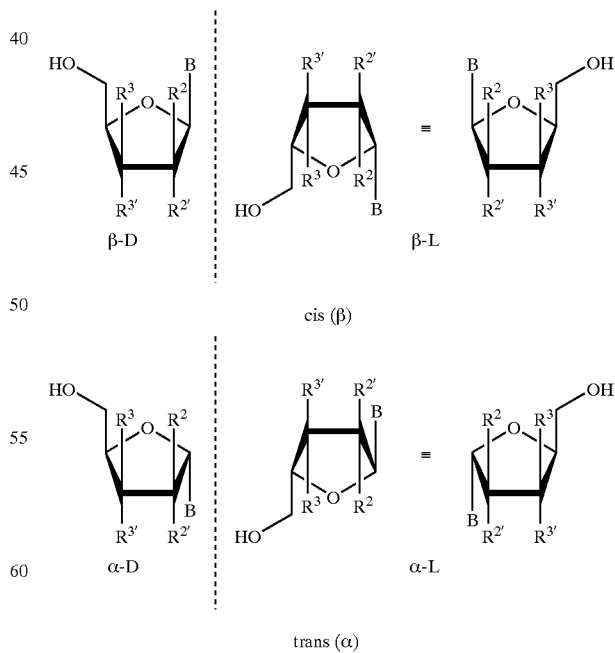

Definitions

As used herein, the term "substantially in the form of a single isomer" or "in isolated form" refers to a 2'-deoxy-β-

L-erythro-pentofuranonucleoside that is at least approximately 95%, and preferably, at least 98% or 99%, in the designated stereoconfiguration. In a preferred embodiment, the active compound is administered in at least this level of purity to the host in need of therapy.

As used herein, the term hepatitis D and related conditions refers to hepatitis D infection, chronic liver inflammation associated with HDV, cirrhosis, acute hepatitis, fulminant hepatitis, chronic persistent hepatitis, and fatigue. The method of the present invention includes the use of 2'-deoxy-β-L-erythro-pentofuranonucleoside derivatives, their pharmaceutically acceptable salts or prodrugs thereof, prophylactically to prevent or retard the progression of clinical illness in individuals who are infected with or who have been exposed to HBV.

As used herein, the term alkyl, unless otherwise specified, refers to a saturated straight, branched, or cyclic, primary, secondary, or tertiary hydrocarbon, typically of $C_1$ to $C_{18}$, preferably $C_1$ to $C_6$ and specifically includes but is not limited to methyl, trifluoromethyl, ethyl, propyl, butyl, pentyl, hexyl, isopropyl, isobutyl, sec-butyl, t-butyl, isopentyl, amyl, t-pentyl, cyclopentyl, and cyclohexyl. The alkyl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference.

As used herein, the term acyl refers to moiety of the formula —C(O)R', wherein R' is alkyl, aryl, alkaryl, aralkyl, heteroaromatic, alkoxyalkyl (including methoxymethyl), arylalkyl (including benzyl), aryloxyalkyl (such as phenoxymethyl) or aryl (including phenyl) optionally substituted with halogen, $C_1$ to $C_4$ alkyl or $C_1$ to $C_4$ alkoxy, or the residue of an amino acid. The term acyl specifically includes but is not limited to acetyl, propionyl, butyryl, pentanoyl, 3-methylbutyryl, hydrogen succinate, 3-chlorobenzoate, benzoyl, acetyl, pivaloyl, mesylate, propionyl, valeryl, caproic, caprylic, capric, lauric, myristic, palmitic, stearic, and oleic, and can also be the residue of an amino acid.

As used herein, the term purine or pyrimidine base, includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolo-pyrimidinyl, and pyrazolopyrimidinyl.

Examples of bases include cytosine, 5-fluorocytosine, 5-bromocytosine, 5-iodocytosine, 5-chlorocytosine, uracil, 5-fluorouracil, 5-bromouracil, 5-iodouracil, 5-methyluracil, thymine, adenine, guanine, inosine, xanthine, 2,6-diaminopurine, 6-aminopurine, 6-chloro-purine and 2,6-dichloropurine, 6-bromopurine, 2,6-dibromopurine, 6-iodopurine, 2,6-di-iodopurine, hypoxanthine, 2-(Br, Fl, Cl or I)-purine optionally with a substituent including an amino or carbonyl group in the 6-position, and 6-(Br, Cl, or I)-purine optionally with a substituent including an amino or carbonyl group in the 2-position, 5-bromovinylcytosine, 5-bromovinyluracil, 5-bromoethenylcytosine, 5-bromoethenyluracil, 5-trifluoromethylcytosine, and 5-trifluoromethyluracil.

The term prodrug, as used herein, refers to a compound that is converted into the nucleoside on administration in vivo. Nonlimiting examples are pharmaceutically acceptable salts (alternatively referred to as "physiologically acceptable salts"), the 5'- and/or the $N^4$ or $N^6$ acylated or alkylated derivatives of the active compound, and the 5'-phospholipid and the 5'-ether lipid derivatives of the active compound.

The term host, as used herein, refers to a unicellular or multicellular organism in which the virus can replicate, including cell lines and animals, and preferably a human. Alternatively, the host can be carrying a part of the hepatitis delta viral genome, whose replication or function can be altered by the compounds of the present invention. The term host specifically refers to infected cells, cells transfected with all or part of the HDV genome and animals, in particular, primates (including chimpanzees) and humans. In most animal applications of the present invention, the host is a human patient. Veterinary applications, in certain indications, however, are clearly anticipated by the present invention (such as chimpanzees).

Pharmaceutically Acceptable Salts and Prodrugs

As used herein, the term pharmaceutically acceptable salts or complexes refers to salts or complexes of the 2'-deoxy-β-L-erythro-pentofuranonucleosides that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acids, naphthalenedisulfonic acids, and polygalacturonic acid; (b) base addition salts formed with cations such as sodium, potassium, zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of (a) and (b); e.g., a zinc tannate salt or the like.

The 2'-deoxy-β-L-erythro-pentofuranonucleoside can be provided as a 5'-phospholipid or a 5'-ether lipid, as disclosed in the following references: Kucera, L. S.; Iyer, N.; Leake, E.; Raben, A.; Modest, E. J.; D. L. W.; and Piantadosi, C. "Novel membrane-interactive ether lipid analogs that inhibit infectious HIV-1 production and induce defective virus formation" *AIDS Res Hum Retroviruses*, 1990, 6, 491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest "Synthesis and evaluation of novel ether lipid nucleoside conjugates for anti-HIV activity" *J Med Chem*, 1991, 34, 1408–1414; Hostetler, K. Y.; Richman, D. D.; Carson, D. A.; Stuhmiller, L. M.; van Wijk, G. M. T.; and van den Bosch, H. "Greatly enhanced inhibition of human immunodeficiency virus type 1 replication in CEM and HT4-6C cells by 31-deoxythymidine diphosphate dimyristoylglycerol, a lipid prodrug of 31-deoxythymidine" *Antimicrob Agents Chemother* 1992, 36, 2025–2029; Hostetler, K. Y., Stuhmiller, L. M.; Lenting, H. B.; van den Bosch, H.; and Richman, D. D. "Synthesis and antiretroviral activity of phospholipid analogs of azidothymidine and other antiviral nucleosides" *J Biol Chem.* 1990, 265, 6112–7.

The 2'-deoxy-β-L-erythro-pentofuranonucleoside can be converted into a pharmaceutically acceptable ester by reaction with an appropriate esterifying agent, for example, an acid halide or anhydride. The nucleoside or its pharmaceutically acceptable prodrug can be converted into a pharmaceutically acceptable salt thereof in a conventional manner, for example, by treatment with an appropriate base or acid. The ester or salt can be converted into the parent nucleoside, for example, by hydrolysis.

Modifications of the active compounds, specifically at the $N^4$, $N^6$ and 5'-O positions, can affect the bioavailability and rate of metabolism of the active species, thus providing control over the delivery of the active species.

A preferred embodiment of the present invention is a method for the treatment of HDV infections in humans or other host animals, that includes administering an effective amount of one or more of a 2'-deoxy-β-L-erythro-pentofuranonucleoside derivative selected from the group consisting of β-L-2'-deoxyadenosine, β-L-2'-deoxycytidine, β-L-2'-deoxyuridine, β-L-2'-guanosine, β-L-2'-deoxyinosine, and β-L-2'-deoxythymidine, or a physiologically acceptable prodrug thereof, including a phosphate, 5' and/or $N^4$ or $N^6$ alkylated or acylated derivative, or a physiologically acceptable salt thereof, optionally in a pharmaceutically acceptable carrier. The compounds of this invention either possess direct anti-HDV activity, or are metabolized to a compound or compounds that exhibit anti-HDV activity. In a preferred embodiment, the 2'-deoxy-β-L-erythro-pentofuranonucleoside is administered substantially in the form of a single isomer, i.e., at least approximately 95% in the designated stereoconfiguration.

Any of the nucleosides described herein can be administered as a stabilized prodrug to increase the activity, bioavailability, stability or other properties that alter the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates (including sugars), 1,2-diacylglycerol and alcohols. Many are described in R. Jones and N. Bischofberger, *Antiviral Research*, 1995, 27, 1–17. Any of these can be used in combination with the disclosed nucleosides to achieve a desired effect.

In one embodiment, the 2'-deoxy-β-L-erythro-pentofuranonucleoside is provided as 5'-hydroxyl lipophilic prodrug. Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.).

Foreign patent applications that disclose lipophilic substituents that can be attached to the 2'-deoxy-β-L-erythro-pentofuranonucleoside derivative of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Additional nonlimiting examples of 2'-deoxy-β-L-erythro-pentofuranonucleosides are those that contain substituents as described in the following publications. These derivatized 2'-deoxy-β-L-erythro-pentofuranonucleosides can be used for the indications described in the text or otherwise as antiviral agents, including as anti-HBV agents (Ho, D. H. W. "Distribution of kinase and deaminase of 1 β-D-arabinofuranosylcytosine in tissues of man and mouse" *Cancer Res* 1973, 33, 2816–2820; Holy, A. "Isopolar phosphorous-modified nucleotide analogues" In: Advances in Antiviral Drug Design, De Clercq (Ed.), JAI Press: 1993, Vol. 1, 179–231; Hong, C. I., Nechaev, A., and West, C. R. "Synthesis and antitumor activity of 1β-D-arabinofuranosylcytosine conjugates of cortisol and cortisone" *Biochem Biophys Rs Commun*, 1979a, 88, 1223–1229; Hong, C. I., Nechaev, A., Kirisits, A. J. Buchheit, D. J. and West, C. R. "Nucleoside conjugates as potential antitumor agents. 3. Synthesis and antitumor activity of 1-(β-D-arabinofuranosyl)cytosine conjugates of corticosteriods and selected lipophilic alcohols" *J Med Chem*, 1980, 28, 171–177; Hostetler, K. Y., Stuhmiller, L. M., Lenting, H. B. M. van den Bosch, H. and Richman, D. D. "Synthesis and antiretroviral activity of phospholipid analogs of azidothymidine and other antiviral nucleosides" *J Biol Chem,* 1990, 265, 6112–6117; Hostetler, K. Y., Carson, D. A. and Richman, D. D. "Phosphatidylazidothymidine: mechanism of antiretroviral action in CEM cells" *J Biol Chem,* 1991, 266, 11714–11717; Hostetler, K. Y., Korba, B. Sridhar, C., Gardener, M. "Antiviral activity of phosphatidyl-dideoxycytidine in hepatitis B-infected cells and enhanced hepatic uptake in mice" *Antiviral Res*, 1994a, 24, 59–67; Hostetler, K. Y., Richman, D. D., Sridhar, C. N. Felgner, P. L, Felgner, J., Ricci, J., Gardener, M. F. Selleseth, D. W. and Ellis, M. N. "Phosphatidylazidothymidine and phosphatidyl-ddC: Assessment of uptake in mouse lymphoid tissues and antiviral activities in human immunodeficiency virus-infected cells and in rauscher leukemia virus-infected mice" *Antimicrobial Agents Chemother* 1994b, 38, 2792–2797; Hunston, R. N., Jones, A. A. McGuigan, C., Walker, R. T., Balzarini, J., and De Clercq, E. "Synthesis and biological properties of some cyclic phosphotriesters derived from 2'-deoxy-5-fluorouridine" *J Med Chem*, 1984, 27, 440–444; Ji, Y. H., Moog, C., Schmitt, G., Bischoff, P. and Luu, B. "Monophosphoric acid diesters of 7β-hydroxycholesterol and of pyrimidine nucleosides as potential antitumor agents: synthesis and preliminary evaluation of antitumor activity" *J Med Chem*, 1990, 33, 2264–2270; Jones, A. S., McGuigan, C., Walker, R. T., Balzarini, J. and DeClercq, E. "Synthesis, properties, and biological activity of some nucleoside cyclic phosphoramidates" *J Chem Soc Perkin Trans I*, 1984, 1471–1474; Juodka, B. A. and Smart, J. "Synthesis of di-ribonucleoside a(P→N) amino acid derivatives" *Coll Czech Chem Comm.* 1974, 39, 363–968; Kataoka, S., Imai, J., Yamaji, N., Kato, M., Saito, M., Kawada, T. and Imai, S. "Alkylated cAMP derivatives; selective synthesis and biological activities" *Nucleic Acids Res Sym Ser*, 1989, 21, 1–2; Kataoka, S., Uchida, R. and Yamaji, N. "A convenient synthesis of adenosine 3',5' cyclic phosphate (cAMP) benzyl and methyl triesters" *Heterocycles*, 1991, 32, 1351–1356; Kinchington, D., Harvey, J. J., O'Connor, T. J., Jones, B. C. N. M., Devine, K. G., Taylor-Robinson, D., Jeffries, D. J. and McGuigan, C. "Comparison of antiviral effects of zidovudine phosphoramidate and phosphorodiamidate derivatives against HIV and MuLV in vitro" *Antiviral Chem Chemother*, 1992, 3, 107–112; Kodama, K., Morozumi, M., Saitoh, K. I., Kuninaka, H., Yoshino, H. and Saneyoshi, M. "Antitumor activity and pharmacology of 1-β-D-arabinofuranosylcytosine-5'-stearylphosphate; an orally active derivative of 1-β-D-arabinofuranosylcytosine" *Jpn J Cancer Res*, 1989, 80, 679–685; Korty, M. and Engels, J. "The effects of adenosine- and guanosine 3',5'-phosphoric and acid benzyl esters on guinea-pig ventricular myocardium" *Naunyn-Schmiedeberg's Arch Pharmacol*, 1979, 310, 103–111; Kumar, A., Goe, P. L., Jones, A. S. Walker, R. T. Balzarini, J. and De Clercq, E. "Synthesis and biological evaluation of some cyclic phosphoramidate nucleoside derivatives" *J Med Chem*, 1990, 33, 2368–2375; LeBec, C., and Huynh-Dinh, T. "Synthesis of lipophilic phosphate triester derivatives of 5-fluorouridine and arabinocytidine as anticancer prodrugs" *Tetrahedron Lett*, 1991, 32, 6553–6556; Lichtenstein,. J., Barner, H. D. and Cohen, S. S. "The metabolism of exogenously supplied nucleotides by *Escherichia coli.*" *J Biol Chem* 1960, 235, 457–465; Lucthy, J., Von Daeniken, A., Friederich, J. Manthey, B., Zweifel, J., Schlatter, C. and Benn, M. H. "Synthesis and toxicological properties of three naturally occurring cyanoepithioalkanes" *Mitt Geg Lebensmittelunters Hyg* 1981, 72, 131–133 (*Chem Abstr*, 95, 127093); McGuigan, C. Tollerfield, S. M. and Riley, P. A. "Synthesis and biological evaluation of some phosphate triester derivatives of the anti-viral drug Ara" *Nucleic Acids Res*, 1989, 17, 6065–6075; McGuigan, C., Devine, K. G., O'Connor, T. J., Galpin, S. A., Jeffries, D. J. and Kinchington, D. "Synthesis and evaluation of some novel phosphoramidate derivatives of 3'-azido-3'-deoxythymidine (AZT) as anti-HIV compounds" *Antiviral Chem Chemother*, 1990a, 1, 107–113; McGuigan, C., O'Connor, T. J., Nicholls, S. R. Nickson, C. and Kinchington, D. "Synthesis and anti-HIV activity of some novel substituted dialkyl phosphate derivatives of AZT and ddCyd" *Antiviral Chem Chemother*, 1990b, 1, 355–360; McGuigan, C., Nicholls, S. R., O'Connor, T. J., and Kinchington, D. "Synthesis of some novel dialkyl phosphate derivative of 3'-modified nucleosides as potential anti-AIDS drugs" *Antiviral Chem Chemother*, 1990c, 1, 25–33; McGuigan, C., Devine, K. G., O'Connor, T. J., and Kinchington, D. "Synthesis and anti-HIV activity of some haloalkyl phosphoramidate derivatives of 3'-azido-3'-deoxythymidine (AZT); potent activity of the trichloroethyl methoxyalaninyl compound" *Antiviral Res*, 1991, 15, 255–263; McGuigan, C., Pathirana, R. N., Mahmood, N., Devine, K. G. and Hay, A. J. "Aryl phosphate derivatives of AZT retain activity against HIV-1 in cell lines which are resistant to the action of AZT" *Antiviral Res*, 1992, 17, 311–321; McGuigan, C., Pathirana, R. N., Choi, S. M., Kinchington, D. and O'Connor, T. J. "Phosphoramidate derivatives of AZT as inhibitors of HIV; studies on the carboxyl terminus" *Antiviral Chem Chemother*, 1993a, 4, 97–101; McGuigan, C., Pathirana, R. N., Balzarini, J. and De Clercq, E. "Intracellular delivery of bioactive AZT nucleotides by aryl phosphate derivatives of AZT" *J Med Chem*, 1993b, 36, 1048–1052.

The question of chair-twist equilibria for the phosphate rings of nucleoside cyclic 3',5'-monophosphates is analyzed by $^1$HNMR and x-ray crystallographic studies of the diastereomers of thymidine phenyl cyclic 3',5'-monophosphate (*J Am Chem Soc*, 109, 4058–4064; Nerbonne, J. M., Richard, S., Nargeot, J. and Lester, H. A. "New photoactivatable cyclic nucleotides produce intracellular jumps in cyclic AMP and cyclic GMP concentrations" *Nature* 1984, 301, 74–76; Neumann, J. M., Hervé, M., Debouzy, J. C., Guerra, F. I., Gouyette, C., Dupraz, B. and Huynh-Dinh, T. "Synthesis and transmembrane transport studies by NMR of a glucosyl phospholipid of thymidine" *J Am Chem Soc*, 1989, 111, 4270–4277; Ohno, R., Tatsumi, N., Hirano, M., Imai, K. Mizoguchi, H., Nakamura, T., Kosaka, M., Takatuski, K., Yamaya, T., Toyama, K., Yoshida, T., Masaoka, T., Hashimoto, S., Ohshima, T., Kimura, I., Yamada, K. and Kimura, J. "Treatment of myelodysplastic syndromes with orally administered 1-β-D-rabinofuranosylcytosine-5'-stearylphosphate" *Oncology*, 1991, 48, 451–455.

Palomino, E., Kessle, D. and Horwitz, J. P. "A dihydropyridine carrier system for sustained delivery of 2',3'-dideoxynucleosides to the brain" *J Med Chem*, 1989, 32, 622–625; Perkins, R. M., Barney, S., Wittrock, R., Clark, P. H., Levin, R. Lambert, D. M., Petteway, S. R., Serafinowska, H. T., Bailey, S. M., Jackson, S., Harnden, M. R. Ashton, R., Sutton, D., Harvey, J. J. and Brown, A. G. "Activity of BRL47923 and its oral prodrug, SB203657A against a rauscher murine leukemia virus infection in mice" *Antiviral Res*, 1993, 20(Suppl. I), 84; Piantadosi, C., Marasco, C. J., Jr., Morris-Natschke, S. L., Meyer, K. L., Gumus, F., Surles, J. R., Ishaq, K. S., Kucera, L. S. Iyer, N., Wallen, C. A., Piantadosi, S. and Modest, E. J. "Synthesis and evaluation of novel ether lipid nucleoside conjugates for anti-HIV-1 activity" *J Med Chem*, 1991, 34, 1408–1414; Pompon, A., Lefebvre, I., Imbach, J. L., Kahn, S. and Farquhar, D. "Decomposition pathways of the mono- and bis (pivaloyloxymethyl) esters of azidothymidine-5'-monophosphate in cell extract and in tissue culture medium; an application of the 'on-line ISRP-cleaning' HPLC technique" *Antiviral Chem Chemother*, 1994, 5, 91–98; Postemark, T. "Cyclic AMP and cyclic GMP" *Annu Rev Pharmacol*, 1974, 14, 23–33; Prisbe, E. J., Martin, J. C. M., McGee, D. P. C., Barker, M. F., Smee, D. F. Duke, A. E., Matthews, T. R. and Verheyden, J. P. J. "Synthesis and anti-herpes virus activity of phosphate and phosphonate derivatives of 9-[(1,3-dihydroxy-2-propoxy)methyl] guanine" *J Med Chem*, 1986, 29, 671–675; Puech, F., Gosselin, G., Lefebvre, I., Pompon, A., Aubertin, A. M. Dirn, A. and Imbach, J. L. "Intracellular delivery of nucleoside monophosphate through a reductase-mediated activation process" *Antiviral Res*, 1993, 22, 155–174; Pugaeva, V. P., Klochkeva, S. I., Mashbits, F. D. and Eizengart, R. S. (1969) Robins, R. K. "The potential of nucleotide analogs as inhibitors of retroviruses and tumors" *Pharm Res*, 1984, 11–18; Rosowsky, A., Kim, S. H., Ross and J. Wick, M. M. "Lipophilic 5'-(alkylphosphate) esters of 1-β-D-arabinofuranosylcytosine and its $N^4$-acyl and 2,2'-anhydro-3'-O-acyl derivatives as potential prodrugs" *J Med Chem*, 1982, 25, 171–178; Ross, W. "Increased sensitivity of the walker turnout towards aromatic nitrogen mustards carrying basic side chains following glucose pretreatment" *Biochem Pharm*, 1961, 8, 235–240; Ryu, E. K., Ross, R. J. Matsushita, T., MacCoss, M., Hong, C. I. and West, C. R. "Phospholipid-nucleoside conjugates. 3. Synthesis and preliminary biological evaluation of 1-β-D-arabinofuranosylcytosine 5'diphosphate[-], 2-diacylglycerols" *J Med Chem*, 1982, 25, 1322–1329; Saffhill, R. and Hume, W. J. "The degradation of 5-iododeoxyuridine and 5-bromodeoxyuridine by serum from different sources and its consequences for the use of these compounds for incorporation into DNA" *Chem Biol*

*Interact*, 1986, 57, 347–355; Saneyoshi, M., Morozumi, M., Kodama, K., Machida, J., Kuninaka, A. and Yoshino, H. "Synthetic nucleosides and nucleotides. XVI. Synthesis and biological evaluations of a series of 1-β-D-arabinofuranosylcytosine 5'-alkyl or arylphosphates" *Chem Pharm Bull*, 1980, 28, 2915–2923; Sastry, J. K., Nehete, P. N., Khan, S., Nowak, B. J., Plunkett, W., Arlinghaus, R. B. and Farquhar, D. "Membrane-permeable dideoxyuridine 5'-monophosphate analogue inhibits human immunodeficiency virus infection" *Mol Pharmacol*, 1992, 41, 441–445; Shaw, J. P., Jones, R. J. Arimilli, M. N., Louie, M. S., Lee, W. A. and Cundy, K. C. "Oral bioavailability of PMEA from PMEA prodrugs in male Sprague-Dawley rats" *9th Annual AAPS Meeting*, San Diego, Calif., 1994 (Abstract). Shuto, S., Ueda, S., Imamura, S., Fukukawa, K. Matsuda, A. and Ueda, T. "A facile one-step synthesis of 5'-phosphatidylnucleosides by an enzymatic two-phase reaction" *Tetrahedron Lett*, 1987, 28, 199–202; Shuto, S., Itoh, H., Ueda, S., Imamura, S., Kukukawa, K., Tsujino, M., Matsuda, A. and Ueda, T. "A facile enzymatic synthesis of 5'-(3-sn-phosphatidyl)-nucleosides and their antileukemic activities" *Chem Pharm Bull*, 1988, 36, 209–217. One preferred phosphate prodrug group is the S-acyl-2-thioethyl group, also referred to as "SATE."

Pharmaceutical Compositions

Pharmaceutical compositions based upon 2'-deoxy-β-L-erythro-pentofuranonucleoside derivatives of the present invention can be prepared that include the above-described compound or its salt or prodrug in a therapeutically effective amount for treating a hepatitis D infection, optionally in combination with a pharmaceutically acceptable additive, carrier or excipient. The therapeutically effective amount may vary with the infection or condition to be treated, its severity, the treatment regimen to be employed, the pharmacokinetics of the agent used, as well as the patient treated.

In one aspect according to the present invention, the compound according to the present invention is formulated preferably in admixture with a pharmaceutically acceptable carrier. In general, it is preferable to administer the pharmaceutical composition in orally administrable form, but formulations may be administered via parenteral, intravenous, intramuscular, transdermal, buccal, subcutaneous, suppository or other route. Intravenous and intramuscular formulations are preferably administered in sterile saline. One of ordinary skill in the art may modify the formulation within the teachings of the specification to provide numerous formulations for a particular route of administration without rendering the compositions of the present invention unstable or compromising its therapeutic activity. In particular, a modification of a desired compound to render it more soluble in water or other vehicle, for example, may be easily accomplished by routine modification (salt formulation, esterification, etc.).

In certain pharmaceutical dosage forms, the prodrug form of the compound, especially including acylated (acetylated or other) and ether derivatives, phosphate esters and various salt forms of the present compounds, is preferred. One of ordinary skill in the art will recognize how to readily modify the present compound to a prodrug form to facilitate delivery of active compound to a targeted site within the host organism or patient. The artisan also will take advantage of favorable pharmacokinetic parameters of the prodrug form, where applicable, in delivering the desired compound to a targeted site within the host organism or patient to maximize the intended effect of the compound in the treatment of hepatitis D infection.

The amount of compound included within therapeutically active formulations, according to the present invention, is an effective amount for treating the infection or condition, in preferred embodiments, a hepatitis D infection. In general, a therapeutically effective amount of the present compound in pharmaceutical dosage form usually ranges from about 0.1 mg/kg to about 100 mg/kg or more, depending upon the compound used, the condition or infection treated and the route of administration. For purposes of the present invention, a prophylactically or preventively effective amount of the compositions, according to the present invention, falls within the same concentration range as set forth above for therapeutically effective amount and is usually the same as a therapeutically effective amount.

Administration of the active compound may range from continuous (intravenous drip) to several oral administrations per day (for example, Q.I.D., B.I.D., etc.) and may include oral, topical, parenteral, intramuscular, intravenous, subcutaneous, transdermal (which may include a penetration enhancement agent), buccal and suppository administration, among other routes of administration. Enteric-coated oral tablets may also be used to enhance bioavailability and stability of the compounds from an oral route of administration. The most effective dosage form will depend upon the pharmacokinetics of the particular agent chosen, as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably mixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated for sustained release by standard techniques. The use of these dosage forms may significantly impact the bioavailability of the compounds in the patient.

For parenteral formulations, the carrier will usually comprise sterile water or aqueous sodium chloride solution, though other ingredients, including those that aid dispersion, also may be included. Where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prodrug forms of the nucleoside compounds according to the present invention.

In particularly preferred embodiments according to the present invention, the compounds and compositions are used to treat, prevent or delay the onset of hepatitis D infections. Preferably, to treat, prevent or delay the onset of infection, the compositions will be administered in oral dosage form in amounts ranging from about 250 micrograms up to about 1 gram or more at least once a day, preferably, or up to four times a day. The present compounds are preferably administered orally, but may be administered parenterally, topically or in suppository form.

The compounds according to the present invention, because of their low toxicity to host cells in certain instances, may be advantageously employed prophylactically to prevent hepatitis D infection or to prevent the occurrence of clinical symptoms associated with the viral infection. Thus, the present invention also encompasses methods for the prophylactic treatment of viral infection, and in particular hepatitis D infection. In this aspect, according to the present invention, the present compositions are used to prevent or delay the onset of a hepatitis D infection. This prophylactic method comprises administration to a patient in need of such treatment, or who is at risk for the development of HDV disease, an amount of a compound according to the present invention effective for alleviating, preventing or delaying the onset of the viral infection. In the prophylactic treatment according to the present invention, it is preferred that the antiviral compound utilized should be low in toxicity and preferably non-toxic to the patient. It is particularly preferred in this aspect of the present invention that the compound that is used should be maximally effective against the virus and should exhibit a minimum of toxicity to the patient. Compounds according to the present invention, which may be used to treat these disease states, may be administered within the same dosage range for therapeutic treatment (i.e., about 250 micrograms up to 1 gram or more from one to four times per day for an oral dosage form) as a prophylactic agent to prevent the proliferation of a hepatitis D infection, or alternatively, to prolong the onset of a hepatitis D infection, which manifests itself in clinical symptoms.

In addition, compounds according to the present invention can be administered in combination or alternation with one or more antiviral, anti-HBV, anti-HCV, anti-HDV or anti-herpetic agent or interferon, anti-cancer or antibacterial agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

Combination or Alternation Therapy

It has been recognized that drug-resistant variants of hepatitis viruses can emerge after prolonged treatment with an antiviral agent. Because of the essential role of hepatitis B virus in the lifecycle of the hepatitis D virus, compounds with anti-hepatitis B virus activity may be administered in combination or alternation with the disclosed β-2'-L-deoxy-nucleosides, their pharmaceutically acceptable salts or prodrugs. Drug resistance most typically occurs by mutation of a gene that encodes for an enzyme used in the viral life cycle, and most typically in the case of HBV, DNA polymerase. Recently, it has been demonstrated that the efficacy of a drug against HBV infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

The anti-hepatitis D viral activity of β-L-2'-dA, β-L-2'-dC, β-L-2'-dU, β-L-2'-dG, β-L-2'-dT, β-L-dI, or other β-L-2'-nucleosides provided herein, or the prodrugs, phosphates, or salts of these compounds, can be enhanced by administering two or more of these nucleosides in combination or alternation. Alternatively, for example, one or more of β-L-2'-dA, β-L-2'-dC, β-L-2'-dU, β-L-2'-dG, β-L-2'-dT, β-L-dI, or other β-L-2'-nucleosides provided herein can be administered in combination or alternation with 3TC, FTC, L-FMAU, DAPD, famciclovir, penciclovir, BMS-200475, bis pom PMEA (adefovir, dipivoxil); lobucavir, ganciclovir, or ribavirin.

In any of the embodiments described herein, if the β-L-2'-nucleoside of the present invention is administered in combination or alternation with a second nucleoside or non-nucleoside polymerase inhibitor that is phosphorylated to an active form, it is preferred that a second compound be phosphorylated by an enzyme that is different from that which phosphorylates the selected β-L-2'-nucleoside of the present invention in vivo. Examples of kinase enzymes are thymidine kinase, cytosine kinase, guanosine kinase, adenosine kinase, deoxycytidine kinase, 5'-nucleotidase, and deoxyguanosine kinase.

Preparation of the Active Compounds

The 2'-deoxy-β-L-erythro-pentofuranonucleoside derivatives of the present invention are known in the art and can be prepared according to the method disclosed by Holy, *Collect Czech Chem Commun*, 1972, 37(12), 4072–87 and *Mol Phys*, 1967, 3(4), 386–95.

A general process for obtaining β-L-erythro-pentafuranonucleosides (β-L-dN) is shown in FIG. 1, using L-ribose or L-xylose as a starting material.

Mono, di, and triphosphate derivatives of the active nucleosides can be prepared as described according to published methods. The monophosphate can be prepared according to the procedure of Imai et al., *J Org Chem*, 1969, 34(6), 1547–1550. The diphosphate can be prepared according to the procedure of Davisson et al., *J Org Chem*, 1987, 52(9), 1794–1801. The triphosphate can be prepared according to the procedure of Hoard et al., *J Am Chem Soc*, 1965, 87(8), 1785–1788.

EXAMPLES

Experimental Protocols

Melting points were determined in open capillary tubes on a Gallenkamp MFB-595-010 M apparatus and are uncorrected. The UV absorption spectra were recorded on an Uvikon 931 (KONTRON) spectrophotometer in ethanol. $^1$H-NMR spectra were run at room temperature in DMSO-$d_6$ with a Bruker AC 250 or 400 spectrometer. Chemical shifts are given in ppm, DMSO-$d_6$ being set at 2.49 ppm as reference. Deuterium exchange, decoupling experiments or 2D-COSY were performed in order to confirm proton assignments. Signal multiplicities are represented by s (singlet), d (doublet), dd (doublet of doublets), t (triplet), q (quadruplet), br (broad), m (multiplet). All J-values are in Hz. FAB mass spectra were recorded in the positive-(FAB>0) or negative-(FAB<0) ion mode on a JEOL DX 300 mass spectrometer The matrix was 3-nitrobenzyl alcohol (NBA) or a mixture (50:50, v/v) of glycerol and thioglycerol (GT). Specific rotations were measured on a Perkin-Elmer 241 spectropolarimeter (path length 1 cm) and are given in units of $10^{-1}$ deg cm$^2$ g$^{-1}$. Elemental analysis were carried out by the "Service de Microanalyses du CNRS, Division de Vernaison" (France). Analyses indicated by the symbols of the elements or functions were within ±0.4% of theoretical

Example 1

9-(3,5-Di-O-benzoyl-β-L-xylofuranosyl)adenine (3)

A solution of 9-(2-O-acetyl-3,5-di-O-benzoyl-β-L-xylofuranosyl)adenine 2 [Ref.: Gosselin, G.; Bergogne, M.-C.; Imbach, J.-L. "Synthesis and Antiviral Evaluation of β-L-Xylofuranosyl Nucleosides of the Five Naturally Occurring Nucleic Acid Bases" *Journal of Heterocyclic Chemistry*, 1993, 30, 1229–1233] (8.30 g, 16.05 mmol) and hydrazine hydrate 98% (234 mL, 48.5 mmol) in a mixture of pyridine/glacial acetic acid (4/1, v/v, 170 mL) was stirred at room temperature for 22 h. The reaction was quenched by adding acetone (40 mL) and stirring was continued for one additional hour. The reaction mixture was reduced to one half of its volume, diluted with water (250 mL) and extracted with chloroform (2×150 mL). The organic layer was washed successively with an aqueous saturated solution of NaHCO$_3$ (3×100 mL) and water (3×100 mL), dried, filtered, concentrated and co-evaporated with toluene and methanol. The residue was purified by silica gel column chromatography (0–3% MeOH in dichloromethane) to give 3 (5.2 g, 68%) precipitated from diisopropylic ether: $^1$H NMR (DMSO-d$_6$): δ 4.5–4.9 (m, 4H, H-2', H-4', H-5' and H-5"), 5.64 (t, 1H, H-3', J$_{2',3'}$=J$_{3',4'}$=3.5 Hz), 6.3 (br s, 1H, OH-2'), 6.45 (d, 1H, H-1', J$_{1',2'}$=4.6 Hz), 7.3 (br s, 2H, NH$_2$-6), 7.4–7.9 (m, 10H, 2 benzoyls), 8.07 and 8.34 (2s, 2H, H-2 and H-8); ms: matrix G/T, (FAB$^+$) m/z 476 [M+H]$^+$, 136 [BH$_2$]$^+$, (FAB$^-$) m/z 474 [M–H]$^-$; 134 [B]$^-$; UV (95% ethanol): λ$_{max}$ 257 nm (ε 16400), 230 nm (ε 29300), λ$_{min}$ 246 nm (ε 14800); [α]$_D^{20}$=–64 (c 1.07, CHCl$_3$). Anal. Calcd for C$_{24}$H$_{21}$N$_5$O$_4$ (M=475.45): C, 60.43; H, 4.45; N, 14.73. Found: C, 60.41; H, 4.68; N, 14.27.

Example 2

9-(3,5-Di-O-benzoyl-2-deoxy-β-L-threo-pentofuranosyl)adenine (4)

To a solution of compound 3 (1.00 g, 2.11 mmol) in dry acetonitrile (65 mL) were added 4-(dimethylamino)pyridine (0.77 g, 6.32 mmol) and phenoxythiocarbonyl chloride (0.44 mL, 3.16 mmol). The mixture was stirred at room temperature for 2 h. After concentration, the residue was dissolved in dichloromethane (50 mL) and washed successively with water (2×30 mL), aqueous solution of hydrochloric acid 0.5 N (30 mL) and water (3×30 mL). The organic layer was dried, filtered and concentrated to dryness. The crude thiocarbonylated intermediate was directly treated with tris-(trimethylsilyl)silane hydride (0.78 mL, 5.23 mmol) and α,α'-azoisobutyronitrile (AIBN, 0.112 g, 0.69 mmol) in dry dioxane (17 mL) at reflux for 2 h. The solvent was removed under vacuum and the residue was purified by silica gel column chromatography (0–5% MeOH in dichloromethane) to give pure 4 (0.93 g, 96%) as a foam: $^1$H NMR (DMSO-d$_6$): δ 2.9–3.1 (m, 2H, H-2' and H-2"), 4.6–4.7 (m, 3H, H-4', H-5' and H-5"), 5.8 (br s, 1H, H-3'), 6.43 (dd, 1H, H-1', J$_{1',2'}$=3.1 Hz, J$_{1',2''}$=7.6 Hz), 7.3 (br s, 2H, NH$_2$-6), 7.4–7.9 (m, 10H, 2 benzoyls), 8.05 and 8.33 (2s, 2H, H-2 and H-8); ms: matrix G/T, (FAB$^+$) m/z 460 [M+H]$^+$, 325 [S]$^+$, 136 [BH$_2$]$^+$, (FAB$^-$) m/z 458 [M–H]$^-$, 134 [B]$^-$; UV (95% ethanol): λ$_{max}$ 261 nm (ε 14400), 231 nm (ε 26300), λ$_{min}$ 249 nm (ε 12000); [α]$_D^{20}$=–38 (c 1.04, DMSO).

Example 3

6-N-(4-Monomethoxytrityl)-9-(3,5-di-O-benzoyl-2-deoxy-β-L-threo-pento-furanosyl)adenine (5)

To a solution of compound 4 (0.88 g, 1.92 mmol) in dry pyridine (40 mL) was added 4-monomethoxytrityl chloride (1.18 g, 3.84 mmol). The mixture was stirred at 60° C. for 24 h. After addition of methanol (5 mL), the solution was concentrated to dryness, the residue was dissolved in dichloromethane (50 mL) and washed successively with water (30 mL), aqueous saturated NaHCO$_3$ (30 mL) and water (30 mL). The organic layer was dried, filtered, concentrated and co-evaporated with toluene to give pure 5 (1.01 g, 72%) as a foam: $^1$H NMR (CDCl$_3$): δ 2.9–3.0 (m, 2H, H-2' and H-2"), 3.62 (s, 3H, OCH$_3$), 4.6–4.8 (m, 3H, H-4', H-5' and H-5"), 5.85 (pt, 1H, H-3'), 6.44 (dd, 1H, H-1', J$_{1',2'}$=3.1 Hz, J$_{1',2''}$=7.3 Hz), 6.9 (br s, 1H, NH-6), 6.7–6.8 and 7.2–7.4 (2m, 24H, 2 benzoyls and MMTr), 7.97 and 8.13 (2s, 2H, H-2 and H-8); ms: matrix G/T, (FAB$^+$) m/z 732 [M+H]$^+$, (FAB$^-$) m/z 730 [M–H]$^-$; UV (95% ethanol): λ$_{max}$ 274 nm (ε 12100), 225 nm (ε 24200), λ$_{min}$ 250 nm (ε 5900); [α]$_D^{20}$=–16 (c 1.12, DMSO).

Example 4

6-N-(4-Monomethoxytrityl)-9-(2-deoxy-β-L-threo-pentofuranosyl)adenine (6)

Compound 5 (0.95 g, 1.30 mmol) was treated with a solution (saturated at –10° C.) of methanolic ammonia (40 mL), at room temperature overnight. After concentration, the residue was dissolved in dichloromethane (60 mL) and washed with water (30 mL). The aqueous layer was extracted twice with dichloromethane (10 mL). The combined organic layer was dried, filtered and concentrated. The residue was purified by silica gel column chromatography (0–5% MeOH in dichloromethane) to give pure 6 (0.67 g, 98%) as a foam: $^1$H NMR (CDCl$_3$): δ 2.6–2.9 (m, 2H, H-2' and H-2"), 3.5 (br s, 1H, OH-5'), 3.55 (s, 3H, OCH$_3$), 3.9–4.0 (m, 3H, H-4', H-5' and H-5"), 4.5–4.6 (m, 1H, H-3'), 6.03 (dd, 1H, H-1', J$_{1',2'}$=4.0 Hz, J$_{1',2''}$=8.8 Hz), 7.0 (br s, 1H, NH-6), 6.7–6.8 and 7.1–7.4 (2m, 14H, MMTr), 7.40 (d, 1H, OH-3', J$_{H,OH}$=10.6 Hz), 7.80 and 7.99 (2s, 2H, H-2 and H-8); ms: matrix G/T, (FAB$^+$) m/z 524 [M+H]$^+$, 408 [BH$_2$]$^+$, (FAB$^-$) m/z 1045 [2M–H]$^-$, 522 [M–H]$^-$, 406 [B]$^-$; UV (95% ethanol): λ$_{max}$ 275 nm (ε 12300), λ$_{min}$ 247 nm (ε 3600); [α]$_D^{20}$=+28 (c 0.94, DMSO).

Example 5

6-N-(4-Monomethoxytrityl)-9-(2-deoxy-5-O-(4-monomethoxytrityl)-β-L-threo-pento-furanosyl)adenine (7)

Compound 6 (0.62 g, 1.24 mmol) in dry pyridine (25 mL) was treated with 4-monomethoxytrityl chloride (0.46 g, 1.49 mmol) at room temperature for 16 h. After addition of methanol (5 mL), the mixture was concentrated to dryness. The residue was dissolved in dichloromethane (60 mL) and washed successively with water (40 mL), a saturated aqueous solution of NaHCO$_3$ (40 mL) and water (3×40 mL). The organic layer was dried, filtered, concentrated and co-evaporated with toluene and methanol. The residue was purified by silica gel column chromatography (0–10% MeOH in dichloromethane) to give 7 (0.71 g, 72%) as a foam: $^1$H NMR (DMSO-d$_6$): δ 2.21 (d, 1H, H-2' J$_{2',2''}$=14.3 Hz), 2.6–2.7 (m, 1H, H-2"), 3.1–3.3 (2m, 2H, H-5' and H-5"), 3.64 and 3.65 (2s, 6H, 2×OCH$_3$), 4.1–4.2 (m, 1H, H-4'), 4.2–4.3 (m, 1H, H-3'), 5.68 (d, 1H, OH-3', J$_{H,OH}$=5.2 Hz), 6.24 (d, 1H, H-1', J$_{1',2''}$=7.0 Hz), 6.7–6.8 and 7.1–7.3 (2m, 29H, 2 MMTr and NH-6), 7.83 and 8.21 (2s, 2H, H-2 and H-8); ms: matrix G/T, (FAB$^+$) m/z 796 [M+H]$^+$, 408 [BH$_2$]$^+$, (FAB$^-$) m/z 794 [M–H]$^-$, 406 [B]$^-$; UV (95% ethanol): λ$_{max}$ 275 nm (ε 30900), λ$_{min}$ 246 nm (ε 12800); [α]$_D^{20}$=+14 (c 1.03, DMSO).

Example 6

6-N-(4-Monomethoxytrityl)-9-(3-O-benzoyl-2-deoxy-5-O-(4-monomethoxytrityl)-β-L-erythro-pentofuranosyl)adenine (8)

A solution of diethylazodicarboxylate (0.38 mL, 2.49 mmol) in dry tetrahydrofuran (20 mL) was added dropwise to a cooled solution (0° C.) of nucleoside 7 (0.66 g, 0.83 mmol), triphenylphosphine (0.66 g, 2.49 mmol) and benzoic acid (0.30 g, 2.49 mmol) in dry THF (20 mL). The mixture was stirred at room temperature for 18 h and methanol (1 mL) was added. The solvents were removed under reduced pressure and the crude material was purified by silica gel column chromatography (0–5% ethyl acetate in dichloromethane) to give compound 8 slightly contaminated by triphenylphosphine oxide.

Example 7

6-N-(4-Monomethoxytrityl)-9-(2-deoxy-5-O-(4-monomethoxytrityl)-β-L-erythro-pentofuranosyl)adenine (9)

Compound 8 was treated by a solution (saturated at –10° C.) of methanolic ammonia (20 mL), at room temperature for 24 h, then the reaction mixture was concentrated to dryness. The residue was dissolved in dichloromethane (30 mL) and washed with water (20 mL). The aqueous layer was extracted by dichloromethane (2×20 mL) and the combined organic phase was dried, filtered and concentrated. Pure compound 9 (0.50 g, 76% from 7) was obtained as a foam after purification by silica gel column chromatography (0–2% MeOH in dichloromethane): $^1$H NMR (DMSO-d$_6$): δ 2.2–2.3 (m, 1H, H-2'), 2.8–2.9 (m, 1H, H-2"), 3.1–3.2 (m, 2H, H-5' and H-5"), 3.64 and 3.65 (2s, 6H, 2×OCH$_3$), 3.97 (pq, 1H, H-4'), 4.4–4.5 (m, 1H, H-3'), 5.36 (d, 1H, OH-3', J$_{H,OH}$=4.5 Hz), 6.34 (t, 1H, H-1', J$_{1',2'}$=J$_{1',2''}$=6.4 Hz), 6.8–6.9 and 7.1–7.4 (2m, 29H, 2 MMTr and NH-6), 7.81 and 8.32 (2s, 2H, H-2 and H-8); ms: matrix G/T, (FAB$^+$) m/z 796 [M+H]$^+$, 408 [BH$_2$]$^+$, (FAB$^-$) m/z 794 [M–H]$^-$, 406 [B]$^-$; UV (95% ethanol): λ$_{max}$ 276 nm (ε 42600), λ$_{min}$ 248 nm (ε 23300); [α]$_D^{20}$=+29 (c 1.05, DMSO).

Example 8

2'-Deoxy-β-L-adenosine (β-L-dA)

Compound 9 (0.44 g, 0.56 mmol) was treated with an aqueous solution of acetic acid 80% (17 mL) at room temperature for 5 h. The mixture was concentrated to dryness, the residue was dissolved in water (20 mL) and washed with diethyl ether (2×15 mL). The aqueous layer was concentrated and co-evaporated with toluene and methanol. The desired 2'-deoxy-β-L-adenosine (β-L-dA) (0.12 g, 83%) was obtained after purification by silica gel column chromatography (0–12% MeOH in dichloromethane) and filtration through a Millex HV-4 unit (0.45μ, Millipore): mp 193–194° C. (crystallized from water) (Lit. 184–185° C. for L-enantiomer [Ref: Robins, M. J.; Khwaja, T. A.; Robins, R. K. J Org Chem 1970, 35, 636–639] and 187–189° C. for D-enantiomer [Ref.: Ness, R. K. in Synthetic Procedures in Nucleic Acid Chemistry Zorbach, W. W., Tipson, R. S., Eds.; J. Wiley and sons: New York, 1968; Vol 1, 183–187]; $^1$H NMR (DMSO-d$_6$): δ 2.2–2.3 and 2.6–2.7 (2m, 2H, H-2' and H-2"), 3.4–3.6 (2m, 2H, H-5' and H-5"), 3.86 (pq, 1H, H-4'), 4.3–4.4 (m, 1H, H-3'), 5.24 (t, 1H, OH-5', J$_{H,OH}$=5.8 Hz), 5.30 (d, 1H, OH-3', J$_{H,OH}$=4.0 Hz), 6.32 (dd, 1H, H-1', J$_{1',2'}$=6.2 Hz, J$_{1',2''}$=7.8 Hz), 7.3 (br s, 2H, NH$_2$-6), 8.11 and 8.32 (2s, 2H, H-2 and H-8); ms: matrix G/T, (FAB$^+$) m/z 252 [M+H]$^+$, 136 [BH$_2$]$^+$, (FAB$^-$) m/z 250 [M–H]$^-$, 134 [B]$^-$, UV (95% ethanol): λ$_{max}$ 258 nm (ε 14300), λ$_{min}$ 226 nm (ε 2100); [α]$_D^{20}$=+25 (c 1.03, H$_2$O), (Lit. [α]$_D^{20}$=+23 (c 1.0, H$_2$O) for L-enantiomer [Ref.: Robins, M. J.; Khwaja, T. A.; Robins, R. K. J Org Chem, 1970, 35, 636–639] and [α]$_D^{20}$=–25 (c 0.47, H$_2$O) for D-enantiomer [Ref.: Ness, R. K. in Synthetic Procedures in Nucleic Acid Chemistry; Zorbach, W. W., Tipson, R. S., Eds.; J. Wiley and sons: New York, 1968; Vol 1, 183–187]). Anal. Calcd for C$_{10}$H$_{13}$N$_5$O$_3$+1.5H$_2$O (M=278.28): C, 43.16; H, 5.80; N, 25.17. Found: C, 43.63; H, 5.45; N, 25.33.

Example 9

1-O-acetyl-2,3,5-tri-O-benzoyl-β-L-ribofuranose (143)

As depicted in Scheme 1, a solution of L-ribose 140 (150 g, 1 mol; Cultor Science Food, CAS [24259-59-4], batch RIB9711013) in methanol (2 liters; P. A. Prolabo; ref 20847.295) was treated with sulphuric acid 95–97% (12 mL; Merck; ref 1.00731.1000) and left at +4° C. for 12 hrs, and then neutralised with pyridine (180 mL; 99% Acros; ref 131780025). Evaporation gave an α,β mixture of methyl ribofuranosides 141 as a syrup. A solution of this anomeric mixture in pyridine (1.3 liters) was treated with benzoyl chloride (580 mL, 5 mol; Fluka; ref 12930) with cooling and mechanical stirring. The solution was left at room temperature for 12 h. and then poured on ice (about 10 liters) with continued stirring. The mixture (an oil in water) was filtered on a Cellite bed. The resulting oil on the cellite bed was washed with water (3×3 liters) and then dissolved with ethyl acetate (3 liters). The organic phase was washed with a 5% NaHCO$_3$ solution (2 liters) and water (2 liters), dried over sodium sulfate (Prolabo; ref 28111.365), filtered and evaporated to give 1-O-methyl-2,3,5-tri-O-benzoyl-α/β-L-ribofuranose 142 as a thick syrup. The oil was dissolved in acetic anhydride (560 mL; Fluka; ref 45830) and acetic acid (240 mL; P. A. carlo erba; ref 20104298). The solution was, after the dropwise addition of concentrated sulphuric acid (80 mL), kept in the cold (+4° C.) under mechanical stirring for 10 h. The solution was then poured on ice (about 10 liters) under continued stirring. The mixture (oily compound in water) was filtered on a Cellite bed. The resulting gummy solid on the cellite bed was washed with water (3×3 liters) and then dissolved in dichloromethane (2.5 liters; P. A. Merck; ref 1.06050.6025). The organic phase was washed with 5% NaHCO$_3$ (1 liter) and water (2×2 liters), dried over sodium sulfate, filtered and evaporated to give a gummy solid 143, which was crystallized from ethanol 95 (Prolabo; ref20823.293) to yield 225 g of product (44%): mp 129–130° C. (EtOH 95) (literature reference reported by Recondo, E. F., and Rinderknecht, H. "Eine neue, Einfache Synthese des 1-O-Acetyl-2,3,5-Tri-O-β-D-Ribofuranosides" Helv. Chim. Acta, 1959, 1171–1173 indicate a mp 130–131° C.); $^1$H NMR (200 MHz, CDCl$_3$): δ

8.09–7.87 (m, 6H, H$_{Arom}$), 7.62–7.31 (m, 9H, H$_{Arom}$) 6.43 (s, 1H, H$_1$), 5.91 (dd, 1H, H$_3$, J$_{3,4}$ 6.7 Hz; J$_{3,2}$ 4.9 Hz), 5.79 (pd, 1H, H$_2$, J$_{2,3}$ 4,9 Hz; J$_{1,2}$ <1), 4.78 (m, 2H, H$_4$ and H$_5$), 4.51 (dd, 1H, H$_5$, J$_{5,5'}$ 13.1 Hz, J$_{5',4}$ 5,5 Hz), 2.00 (s, 3H, CH$_3$CO); (identical to commercial 1-O-acetyl-2,3,5-tri-O-benzoyl-β-D-ribofuranose), Mass analysis (FAB$^+$, GT) m/z 445 (M–OAc)$^+$, Elemental analysis C$_{28}$H$_{24}$O$_9$ Calculated C, 66.66; H, 4.79; found C H.

Scheme 1:

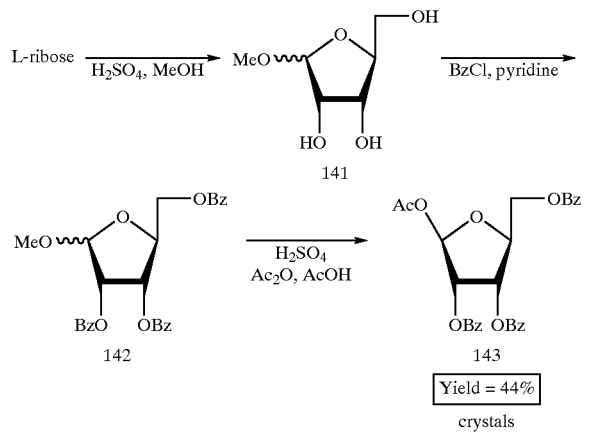

Example 10

β-L-adenosine (145)

As depicted in Scheme 2, adenine (19.6 g, 144 mmol; Pharma-Waldhof; ref 400134.001 lot 45276800) was suspended in acetonitrile (400 mL; Riedel-de Hean; ref 33019; distilled over CaH$_2$) with 1-O-acetyl-2,3,5-tri-O-benzoyl-β-L-ribofuranose 143 (60 g, 119 mmol). To this suspension was added fuming stannic chloride (22 mL, 187 mmol; Fluka; ref 96558). After 12 hrs, the reaction was concentrated to a small volume (about 100 mL); sodium bicarbonate (110 g) and water (120 mL) were added. The resulting white solid (tin salts) was extracted with hot chloroform (5×200 mL; Acros; ref 22706463). The combined extracts were filtered on a cellite bed. The organic phase was washed with a NaHCO$_3$ 5% solution and water, dried over sodium sulfate (Prolabo; ref 28111.365), filtered and evaporated to give compound 144 (60 g, colorless foam). The foam was treated with methanol saturated with ammonia (220 mL) in sealed vessel at room temperature under stirring for 4 days. The solvent was evaporated off under reduced pressure and the resulting powder was suspended in ethyl acetate (400 ml; Carlo erba; ref 528299) at reflux for 1 hr. After filtration, the powder was recrystallized from water (220 mL) to give L-adenosine 145 (24 g, crystals, 75%): mp 233–234° C. (Saneyoshi, M., and Satoh, E. "Synthetic Nucleosides and Nucleotides. XIII. Stannic Chloride Catalyzed Ribosylation of Several 6-Substituted Purines" Chem Pharm Bull, 1979, 27, 2518–2521; Nakayama, C., and Saneyoshi, M. "Synthetic Nucleosides and Nucleotides. XX. Synthesis of Various 1-β-Xylofuranosyl-5-Alkyluracils and Related Nucleosides" Nucleosides Nucleotides, 1982, 1, 139–146 report mp of 235°–238° C.); $^1$H NMR (200 MHz, DMSO-D$_6$): δ 8.34 and 8.12 (2s, 2H, H$_2$ and H$_8$), 7.37 (1s, 2H, NH$_2$), 5.86 (d, 1H, H$_1$, J$_{1',2'}$ 6.2 Hz), 5.43 (m, 2H, OH$_2$ and OH$_5$), 5.19 (d, 1H, OH$_3$, J 3.7 Hz), 4.60 (m, H$_2$), 4.13 (m, 1H, H$_3$), 3.94 (m, 1H, H$_4$), 3.69–3.49 (m, 2H, H$_{5'a}$ and H$_{5'b}$), (identical to commercial D-adenosine); Mass analysis (FAB+, GT) m/z 268 (M+H)$^+$, 136(BH$_2$)$^+$.

Scheme 2:

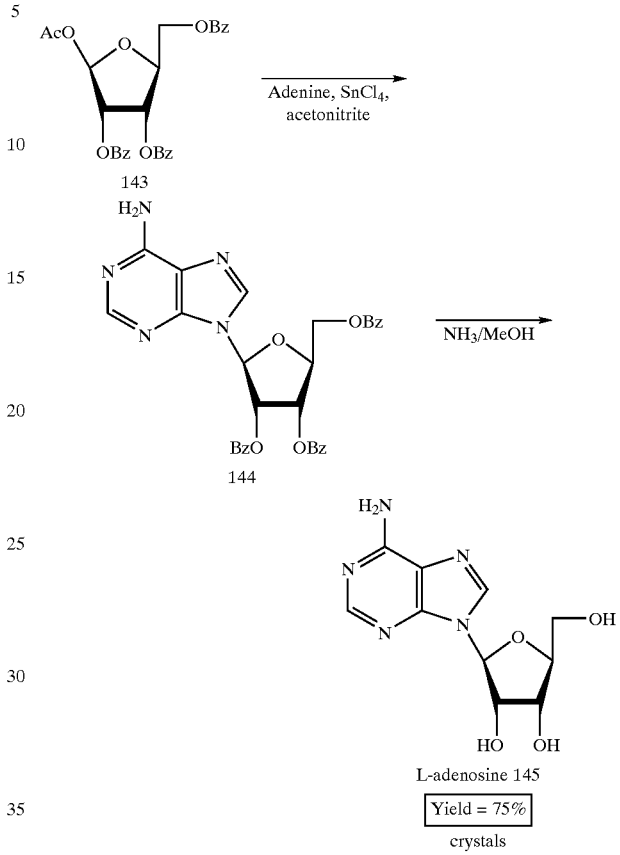

Example 11

3',5'-O-(1,1,3,3-tetraisopropyl-1,3-disiloxanyl)-β-L-adenosine (146)

As shown in Scheme 3, L-adenosine 145 (47.2 g, 177 mmol) is suspended in pyridine (320 mL; 99% from Acros; ref 131780025) was added 1,3-dichloro-1,1,3,3-tetraisopropyl-disiloxane (63 mL, 201 mmol; Fluka; ref 36520), and the mixture was stirred at room temperature for 12 hrs. Pyridine was evaporated and the residue was partitioned with ethyl acetate (1 L; Carlo erba; ref 528299) and a NaHCO$_3$ 5% solution (600 mL). The organic phase was washed with a HCl 0.5N solution (2×500 mL) and water (500 mL), dried over sodium sulfate (Prolabo; ref 28111.365), filtered and evaporated to dryness. The resulting solid was crystallized from acetonitrile (Riedel-de Haen; ref 33019) to give compound 146 (81 g, 90%): mp 97–98° C. (Robins, M. J., et al. "Nucleic Acid Related Compounds. 42. A General Procedure for the Efficient Deoxygenation of Secondary Alcohols. Regiospecific and Stereoselective Conversion of Ribonucleosides to 2'-Deoxynucleosides" J Am Chem Soc, 1983, 105, 4059–4065 reports for the D enantiomer a mp of 98° C.); $^1$H NMR (200 MHz, CDCl$_3$): δ 8.28 and 7.95 (2s, 2H, H$_2$ and H$_8$), 5.96 (d, 1H, J$_{1',2'}$ 1.1 Hz), 5.63 (s, 2H, NH$_2$), 5.10 (dd, 1H, H$_3$, J$_{3',4'}$ 7.6 Hz, J$_{3',2'}$ 5.5 Hz), 4.57 (dd, 1H, H$_2$, J$_{2',1'}$ 1.2 Hz; J$_{2',3'}$ 7.6 Hz), 4.15–3.99 (m, 3H, H$_4$, H$_{5'a}$ and H$_{5'b}$), 3.31 (s1, 1H, OH$_2$), 1.06 (m, 28H, isopropyl protons); Mass analysis (FAB–, GT) m/z 508

(M–H)⁻, 134 (B)⁻; (FAB+, GT) m/z 510 (M+H)⁺, 136 (BH₂)⁺.

Scheme 3:

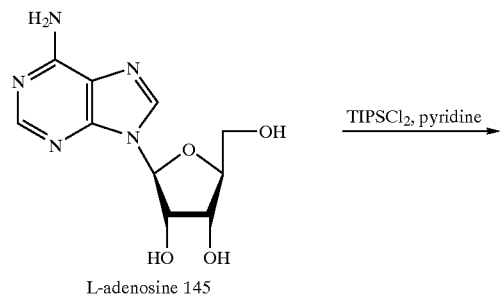

L-adenosine 145

146
Yield = 90%
crystals

Example 12

3',5'-O-(1,1,3,3-tetraisopropyl-1,3-disiloxanyl)-2'-deoxy-β-L-adenosine (148)

To compound 146 (34 g, 67 mmol) was added acetonitrile (280 mL; Riedel-de Haen; ref 33019), DMAP (16.5 g, 135 mmol; 99% from Acros; ref 1482702050) and phenyl chlorothionocarbonate (10.2 mL, 73 mmol; 99% from Acros; ref 215490050), as shown in Scheme 4. The solution was stirred at room temperature for 12 hrs. Solvent was evaporated and the residue was portioned between ethyl acetate (400 mL; Carlo Erba; ref 528299) and a HCl 0.5N solution (400 mL). The organic layer was washed with a HCl 0.5N solution (400 mL) and water (2×400 mL), dried over sodium sulfate (Prolabo; ref 28111.365), filtered and evaporated to dryness to give the intermediate as a pale yellow solid. The crude 147 was dissolved in dioxan (Merck; ref 1.09671.1000) and AIBN (3.3 g, 20 mmol; α,α'-azoisobutyronitrile from Fluka, ref 11630) and TTMSS (33 mL, 107 mmol; tris (trimethylsilyl)silane from Fluka; ref 93411) were added. The solution was progressively heated until reflux and stirred for 2 hrs. The reaction was concentrated to a yellow oil which was chromatographed (eluent dichloromethane (Merck; ref 1.06050.6025): methanol (Carlo Erba; ref 309002) 95:5) to give compound 148 (23 g, colorless foam, 70%). An aliquot was cristallized from ethanol/petroleum ether: mp 110–111° C. (Robins, M. J., Wilson, J. S., and Hansske, F. "Nucleic Acid Related Compounds. 42. A General Procedure for the Efficient Deoxygenation of Secondary Alcohols. Regiospecific and Stereoselective Conversion of Ribonucleosides to 2'-Deoxynucleosides" *J Am Chem Soc*, 1983, 105, 4059–4065 report mp 113–114° C.); ¹H NMR (200 MHz, CDCl₃): δ 8.33 and 8.03 (2s, 2H, H₂ and H₈), 6.30 (dd, 1H, H₁', J 2.85 Hz, J 7.06 Hz), 5.63 (s1, 2H, NH₂), 4.96 (m, 1H, H₃'), 4.50 (m, 2H, H₅'ₐ and H₅'ᵦ), 2.68 (m, 2H, H₂'ₐ and H₂'ᵦ), 1.08 (m, 28H, isopropyl protons); Mass analysis (FAB+, GT) m/z 494 (M+H)⁺, 136 (BH₂)⁺.

Scheme 4:

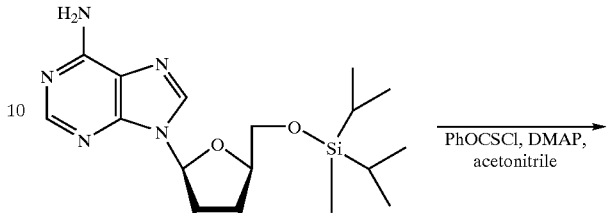

146

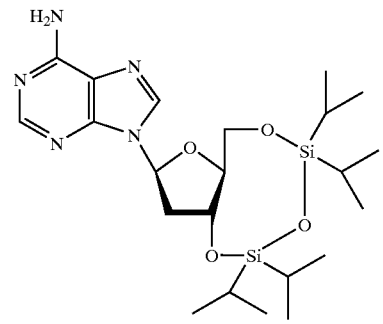

147

148
1 chromatography column
Yield = 70%
foam

Example 13

2'-Deoxy-β-L-adenosine (149)

As taught by Zhang, W., and Robins, M. J. "Removal of Silyl Protecting Groups from Hydroxyl Functions with Ammonium Fluoride in Methanol" *Tetrahedron Lett*, 1992, 33, 1177–1180, a solution of 3',5'-O-(1,1,3,3-tetraisopropyl-1,3-disiloxanyl)-2'-deoxy-L-adenosine 148 (32 g, 65 mmol) and ammonium fluoride (32 g, mmol; Fluka; ref 09742) in methanol (Prolabo; ref 20847.295) was stirred at reflux for 2 hrs (Scheme 5). Silica gel (Merck; ref 1.07734.2500) was added and the mixture was carefully evaporated to give a white powder. This powder was added on the top of a silica column, which was eluted with dichloromethane (Merck; ref 1.06050.6025)/methanol 9/1. The appropriate fractions were combined and evaporated to give a white powder, which was crystallized from ethanol 95 (Prolabo; ref 20823.293) to yield 12.1 g of product (75%): mp 189–190° C. (EtOH 95) (identical to commercial 2'-deoxy-D-adenosine); $^1$H NMR (200 MHz, DMSO-$D_6$): δ 8.35 and 8.14 (2s, 2H, $H_2$ and $H_8$), 7.34 (s1, 2H, $NH_2$), 6.35 (dd, 1H, $H_{1'}$, J 6.1 Hz, J 7.85 Hz), 5.33 (d, 1H, $OH_{2'}$, J 4.0 Hz), 5.28 (dd, 1H, $H_{3'}$, J 4.95 Hz; J 6.6 Hz), 4.42 (m, 1H, OH5'), 3.88 (m, 1H, $H_{4'}$), 3.63–3.52 (m, 2H, $H_{5'a}$ and $H_{5'b}$), 2.71 (m, 1H, $H_{2'a}$), 2.28 (m, 1H, $H_{2'b}$). (identical to commercial 2'-deoxy-D-adenosine); $α_D$ +26° (c 0.5 water) (commercial 2'-deoxy-D-adenosine −25° (c 0.5 water)); UV λmax 260 nm (ε 14100) ($H_2O$); Mass analysis (FAB+, GT) m/z 252 (M+H)$^+$, 136 ($BH_2$)$^+$.

Scheme 5:

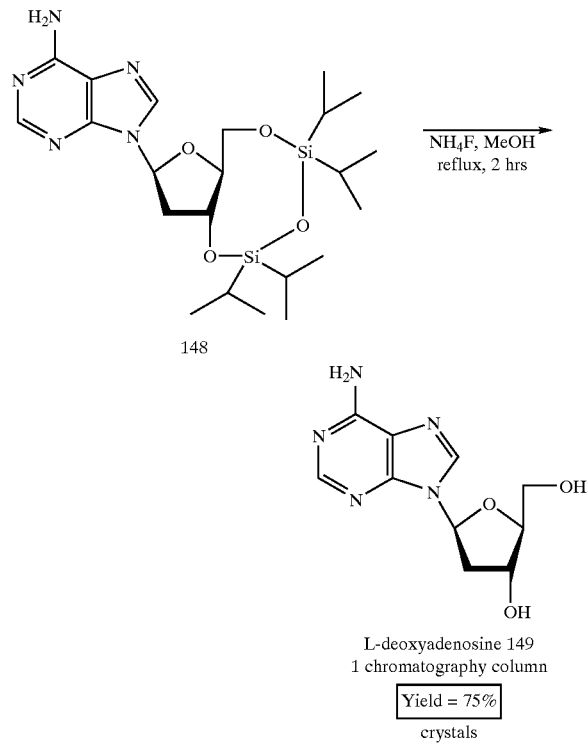

148

L-deoxyadenosine 149
1 chromatography column

Yield = 75%
crystals

Example 14

1-(3,5-Di-O-benzoyl-β-L-xylofuranosyl)uracil (11)

Hydrazine hydrate (1.4 mL, 28.7 mmol) was added to a solution of 1-(2-O-acetyl-3,5-di-O-benzoyl-β-L-xylofuranosyl)uracil 10 [Gosselin, G.; Bergogne, M.-C. and Imbach, J.-L. "Synthesis and Antiviral Evaluation of β-L-Xylofuranosyl Nucleosides of the Five Naturally Occurring Nucleic Acid Bases" *Journal of Heterocyclic Chemistry*, 1993, 30, 1229–1233] (4.79 g, 9.68 mmol) in pyridine (60 mL) and acetic acid (15 mL). The solution was stirred overnight at room temperature. Acetone was added (35 mL) and the mixture was stirred for 30 min. The reaction mixture was evaporated under reduced pressure. The resulting residue was purified by silica gel column chromatography [eluent: stepwise gradient of methanol (0–4%) in dichloromethane to give 11 (3.0 g, 68%) which was crystallized from cyclohexane/dichloromethane: mp=111–114° C.; $^1$H-NMR (DMSO-$d_6$): δ 11.35 (br s, 1H, NH), 7.9–7.4 (m, 11H, 2 $C_6H_5CO$, H-6), 6.38 (d, 1H, OH-2', $J_{OH-2'}$=4.2 Hz), 5.77 (d, 1H, H-1', $J_{1'-2'}$=1.9 Hz), 5.55 (d, 1H, H-5, $J_{5-6}$=8 Hz), 5.54 (dd, 1H, H-3', $J_{3'-2'}$=3.9 Hz and $J_{3'-4'}$=1.8 Hz), 4.8 (m, 1H, H-4'), 4.7 (m, 2H, H-5' and H-5"), 4.3 (m, 1H, H-2'); MS: FAB>0 (matrix GT) m/z 453 (M+H)$^+$, 105 ($C_6H_5CO$)$^+$; FAB<0 (matrix GT) m/z 451 (M−H)$^-$, 121 ($C_6H_5CO_2$)$^-$, 111 (B)$^-$; Anal. Calcd for $C_{23}H_{20}N_2O_8 \cdot H_2O$: C, 58.09; H, 4.76; N, 5.96. Found: C, 57.71; H, 4.42; N, 5.70.

Example 15

1-(3,5-Di-O-benzoyl-β-L-arabinofuranosyl)uracil (12)

To a solution of 1-(3,5-di-O-benzoyl-β-L-xylofuranosyl) uracil 11 (8 g, 17.7 mL) in an anhydrous benzene-DMSO mixture (265 mL, 6:4, v/v) were added anhydrous pyridine (1.4 mL), dicyclohexylcarbodiimide (10.9 g, 53 mmol) and dichloroacetic acid (0.75 mL). The resulting mixture was stirred at room temperature for 4 h, then diluted with ethyl acetate (400 mL) and a solution of oxalic acid (4.8 g, 53 mmol) in methanol (14 mL) was added. After being stirred for 1 h, the solution was filtered. The filtrate was washed with a saturated NaCl solution (2×500 mL), 3% $NaHCO_3$ solution (2×500 mL) and water (2×500 mL). The organic phase was dried over $Na_2SO_4$, then evaporated under reduced pressure. The resulting residue was then solubilized in an absolute EtOH/benzene mixture (140 mL, 2:1, v/v). To this solution at 0° C. was added $NaBH_4$ (0.96 g, 26.5 mmol). After being stirred for 1 h, the solution was diluted with ethyl acetate (400 mL), then filtered. The filtrate was washed with a saturated NaCl solution (400 mL) and water (400 mL). The organic phase was dried over $Na_2SO_4$, then evaporated under reduced pressure. The resulting crude material was purified by silica gel column chromatography [eluent: stepwise gradient of methanol (0–3%) in dichloromethane to give 12 (5.3 g, 66%) which was crystallized from acetonitrile: mp=182–183° C.; $^1$H-NMR (DMSO-$d_6$): δ 11.35 (br s, 1H, NH), 8.0–7.5 (m, 11H, 2 $C_6H_5CO$, H-6), 6.23 (br s, 1H, OH-2'), 6.15 (d, 1H, H-1', $J_{1'-2'}$=4 Hz), 5.54 (d, 1H, H-5, $J_{5-6}$=8.1 Hz), 5.37 (t, 1H, H-3', $J_{3'-2'}$=$J_{3'-4'}$=2.6 Hz), 4.7–4.6 (m, 2H, H-5' and H-5"), 4.5 (m, 1H, H-4'), 4.4 (m, 1H, H-2'); MS: FAB>0 (matrix GT) m/z 453 (M+H)$^+$, 341 (S)$^+$, 113 ($BH_2$)$^+$, 105 ($C_6H_5CO$)$^+$; FAB<0 (matrix GT) m/z 451 (M−H)$^-$, 121 ($C_6H_5CO_2$)$^-$, 111 (B)$^-$; Anal. Calcd for $C_{23}H_{20}N_2O_8$: C, 61.06; H, 4.46; N, 6.19. Found: C, 60.83; H, 4.34; N, 6.25.

Example 16

1-(3,5-Di-O-benzoyl-2-deoxy-β-L-erythro-pentofuranosyl)uracil (13)

To a solution of 1-(3,5-di-O-benzoyl-β-L-arabinofuranosyl)uracil 12 (5.2 g, 11.4 mmol) in anhydrous 1,2-dichloroethane (120 mL) were added phenoxythiocarbonyl chloride (4.7 mL, 34.3 mL) and 4-(dimethylamino) pyridine (DMAP, 12.5 g, 102.6 mmol). The resulting solution was stirred at room temperature under argon atmosphere for 1 h and then evaporated under reduced pressure. The residue was dissolved in dichloromethane (300 mL) and the organic solution was successively washed with an ice-cold 0.2 N hydrochloric acid solution (3×200 mL) and water (2×200 mL), dried over $Na_2SO_4$ then evaporated under reduced pressure. The crude material was coevaporated several times with anhydrous dioxane and dissolved in this solvent (110 mL). To the resulting solution were added under argon tris-(trimethylsilyl)silane hydride (4.2 mL, 13.7 mmol) and α,α'-azoisobutyronitrile (AIBN, 0.6 g, 3.76 mmol). The reaction mixture was heated and stirred at 100° C. for 1 h under argon, then cooled to room temperature and evaporated under reduced pressure. The residue was purified by silica gel column chromatography [eluent: stepwise gradient of methanol (0–5%)] to give 13 (2.78 g, 56%) which was crystallized from EtOH: mp=223–225° C.; H-NMR (DMSO-d$_6$): δ 11.4 (br s, 1H, NH), 8.0–7.5 (m, 11H, 2 C$_6$H$_5$CO, H-6), 6.28 (t, 1H, H-1', J=7 Hz), 5.5 (m, 2H, H-1' and H-5), 4.6–4.4 (m, 3H, H-4', H-5' and H-5"), 2.6 (m, 2H, H-2' and H-2"); MS: FAB>0 (matrix GT) m/z 437 (M+H)$^+$, 3325 (S)$^+$; FAB<0 (matrix GT) m/z 435 (M−H)$^−$, 111 (B)$^−$; Anal. Calcd for C$_{23}$H$_{20}$N$_2$O$_7$: C, 63.30; H, 4.62; N, 6.42. Found: C, 62.98; H, 4.79; N, 6.40.

Example 17

2'-Deoxy-β-L-cytidine (β-L-dC)

Lawesson's reagent (1.72 g, 4.26 mmol) was added under argon to a solution of 1-(3,5-di-O-benzoyl-2-deoxy-β-L-erythro-pentofuranosyl)uracil 13 (2.66 g, 6.1 mmol) in anhydrous 1,2-dichloroethane (120 mL) and the reaction mixture was stirred under reflux for 2 h. The solvent was then evaporated under reduced pressure and the residue was purified by silica gel column chromatography [eluent: stepwise gradient of ethyl acetate (0–8%) in dichloromethane] to give the 4-thio intermediate as a yellow foam. A solution of this thio-intermediate (1.5 g, 3.31 mmol) in methanolic ammonia (previously saturated at −10° C. and tightly stopped) (50 mL) was heated at 100° C. in a stainless-steel bomb for 3 h and then cooled to 0° C. The solution was evaporated under reduced pressure. The resulting crude material was purified by silica gel column chromatography [eluent: stepwise gradient of methanol(0–20%) in dichloromethane]. Finally, the appropriate fractions were pooled, filtered through a unit Millex HV-4 (0.45 μm, Millipore) and evaporated under reduced pressure to provide the desired 2'-deoxy-β-L-cytidine (β-L-dC) as a foam (0.6 g, 80%) which was crystallized from absolute EtOH: mp=198–199° C.; $^1$H-NMR (DMSO-d$_6$): δ 7.77 (d, 1H, H-6, J$_{6-5}$=7.4 Hz), 7.10 (br d, 2H, NH-$_2$), 6.13 (t, 1H, H-1', J=6.7 Hz), 5.69 (d, 1H, H-5, J$_{5-6}$=7.4 Hz), 5.19 (d, 1H, OH-3', J$_{OH-3'}$=4.1 Hz), 4.96 (t, 1H, OH-5', J$_{OH-5'}$=J$_{OH-5"}$=5.2 Hz), 4.1 (m, 1H, H-3'), 3.75 (m, 1H, H-4'), 3.5 (m, 2H, H-5' and H-5"), 2.0 (m, 1H, H-2'), 1.9 (m, 1H, H-2"); MS: FAB>0 (matrix GT) m/z 228 (M+H)$^+$, 112 (BH$_2$)$^+$; FAB<0 (matrix GT) m/z 226 (M−H)$^−$; [α]$^{20}_D$=−69 (c 0.52, DMSO) [[α]$^{20}_D$=+76 (c 0.55, DMSO) for a commercially available hydrochloride salt of the D-enantiomer]. Anal. Calcd for C$_9$H$_{13}$N$_3$O$_4$: C, 47.57; H, 5.77; N, 18.49. Found: C, 47.35; H, 5.68; N, 18.29.

Example 18

2-Amino-β-L-arabinofurano[1',2':4,5]oxazoline (151)

A mixture of L-arabinose (170 g, 1.13 mol; Fluka, >99.5%, ref 10839), cyanamide (100 g, 2.38 mol; Fluka, >98%, ref 28330), methanol (300 mL), and 6M-NH$_4$OH (50 mL) was stirred at room temperature for 3 days and then kept at −10° C. overnight. The product was collected with suction, washed successively with methanol and ether, and dried in vacuo. Yield, 130 g (66.0%) of the analytically pure compound 151 m.p. 170–172° C.; $^1$H NMR (DMSO-d$_6$) δ ppm 6.35 (br s, 2H, NH$_2$), 5.15 (d, 1H, H-1, J=5.6 Hz), 5.45 (br s, 1H, OH-3), 4.70 (br s, 1H, OH-5), 4.55 (d, 1H, H-2, J=5.6 Hz), 4.00 (br s, 1H, H-3), 3.65 (m, 1H, H-4), 3.25 (m, 2H, H-5, H-5').

Example 19

O$^{2,2'}$-anhydro-β-L-uridine (152)

A solution of compound 151 (98.8 g, 0.57 mol) and methyl propiolate (98 mL; Fluka, >97%, ref 81863) in 50% aqueous ethanol (740 mL) was refluxed for 5 h, then cooled and concentrated under diminished pressure to the half of the original volume. After precipitation with acetone (600 mL), the product was collected with suction, washed with ethanol and ether, and dried. The mother liquor was partially concentrated, the concentrate precipitated with acetone (1000 mL), the solid collected with suction, and washed with acetone and ether to afford another crop of the product. Overall yield, 80 g (62%) of compound 152 m.p. 236–240° C.; $^1$H NMR (DMSO-d$_6$) δ ppm 7.87 (d, 1H, H-6, J=7.4 Hz), 6.35 (d, 1H, H-1', J=5.7 Hz), 5.95 (d, 1H, H-5, J=7.4 Hz), 5.90 (d, 1H, OH-3'), 5.20 (d, 1H, H-2', J=5.7 Hz), 5.00 (m, 1H, OH-3'), 4.44 (br s, 1H, H-3'), 4.05 (m, 1H, H-4'), 3.25 (m, 2H, H-5, H-5').

Example 20

3',5'-Di-O-benzoyl-O$^{2,2'}$-anhydro-β-L-uridine (153)

To a solution of compound 152 (71.1 g, 0.31 mol) in anhydrous pyridine (1200 mL) was added benzoyl chloride (80.4 mL; Fluka, p.a., ref 12930) at 0° C. and under argon. The reaction mixture was stirred at room temperature for 5 h under exclusion of atmospheric moisture and stopped by addition of ethanol. The solvents were evaporated under reduced pressure and the resulting residue was co-evaporated with toluene and absolute ethanol. The crude mixture was then diluted with ethanol and the precipitate collected with suction, washed successively with ethanol and ether, and dried. Yield, 129 g (95.8%) of compound 153, m.p. 254° C.; $^1$H NMR (DMSO-d$_6$) δ ppm 8.1–7.4 (m, 11H, C$_6$H$_5$CO, H-6), 6.50 (d, 1H, H-1', J=5.7 Hz), 5.90 (d, 1H, H-5, J=7.5 Hz), 5.80 (d, 1H, H-2', J=5.8 Hz), 5.70 (d, 1H, H-3') 4.90 (m, 1H, H-4'), 4.35 (m, 2H, H-5, H-5').

Example 21

3',5'-Di-O-benzoyl-2'-chloro-2'-deoxy-β,L-uridine (154)

To a solution of compound 153 (60.3 g, 0.139 mol) in dimethylformamide (460 mL) was added at 0° C. a 3.2 N-HCl/DMF solution (208 mL, prepared in situ by adding 47.2 mL of acetyl chloride (Fluka, p.a., ref 00990) at 0° C. to a solution of 27.3 mL of methanol and 133.5 mL of dimethylformamide). The reaction mixture was stirred at 100° C. for 1 h under exclusion of atmospheric moisture, cooled down, and poured into water (4000 mL). The precipitate of compound 154 was collected with suction, washed with water, and recrystallized from ethanol. The crystals were collected, washed with cold ethanol and ether, and dried under diminished pressure. Yield, 60.6 g (92.6%) of compound 154, m.p. 164–165° C.; $^1$H NMR (DMSO-d$_6$) δ ppm 8.7 (br s, 1H, NH), 8.1–7.3 (m, 11H, C$_6$H$_5$CO, H-6), 6.15 (d, 1H, H-1', J=4.8 Hz), 5.5 (m, 2H, H-5, H-2'), 4.65 (m, 4H, H-3', H-4', H-5', H-5").

Example 22

3',5'-Di-O-benzoyl-2'-deoxy-β,L-uridine (155)

A mixture of compound 154 (60.28 g, 0.128 mol), tri-n-butyltin hydride (95 mL; Fluka, >98%, ref 90915) and azabisisobutyronitrile (0.568 g; Fluka, >98%, ref 11630) in dry toluene (720 mL) was refluxed under stirring for 5 h and cooled down. The solid was collected with suction and washed with cold toluene and petroleum ether. The filtrate was concentrated under reduced pressure and diluted with petroleum ether to deposit an additional crop of compound 155. Yield, 54.28 g (97.2%) of compound 155; m.p. 220–221° C.; $^1$H NMR (CDCl$_3$) δ ppm 8.91 (br s, 1H, NH), 8.1–7.5 (m, 11H, C$_6$H$_5$CO and H-6), 6.43 (q, 1H, H-1', J$_{1',2'}$=5.7 Hz and J$_{1',2''}$=8.3 Hz), 5.7–5.6 (m, 2H, H-3' and H-5), 4.8–4.6 (m, 3H, H-5', H-5" and H-4'), 2.8–2.7 (m, 1H, H-2'), 2.4–2.3 (m, 1H, H-2").

Example 23

3',5'-Di-O-benzoyl-2'-deoxy-β-L-4-thio-uridine (156)

A solution of compound 155 (69 g, 0.158 mol) and Lawesson's reagent (74 g; Fluka, >98%, ref 61750) in anhydrous methylene chloride (3900 mL) was refluxed under argon overnight. After evaporation of the solvent, the crude residue was purified by a silica gel column chromatography [eluent: gradient of methanol (0–2%) in methylene chloride] to afford pure compound 156 (73 g) in quantitative yield; $^1$H NMR (CDCl$_3$) δ ppm 9.5 (br s, 1H, NH), 8.1–7.4 (m, 10H, C$_6$H$_5$CO), 7.32 (d, 1H, H-6, J=7.7 Hz), 6.30 (dd, 1H, H-1', J=5.6 Hz and J=8.2 Hz), 6.22 (d, 1H, H-5, J=7.7 Hz), 5.6 (m, 1H, H-3'), 4.7 (m, 2H, H-5', H-5"), 4.5 (m, 1H, H-4'), 2.8 (m, 1H, H-2'), 2.3 (m, 1H, H-2").

Example 24

2'-Deoxy-β-L-cytosine

A solution of compound 156 (7.3 g, 0.016 mol) in methanol saturated with ammonia (73 mL) was heated at 100° C. in a stainless steel cylinder for 3 h. After cooling carefully, the solvent was evaporated under reduced pressure. An aqueous solution of the residue was washed with ethyl acetate and evaporated to dryness. Such a procedure was carried out on 9 other samples (each 7.3 g) of compound 156 (yield of 2'-deoxy-β-L-cytosine: 73 g). The 10 residues were combined, diluted with absolute ethanol and cooled to give 2'-deoxy-β-L-cytosine as crystals. Traces of benzamide were eliminated from the crystals of 2'-deoxy-β-L-cytosine by a solid-liquid extraction procedure (at reflux in ethyl acetate for 1 h). Yield, 28.75 g (78.6%) of compound 2'-deoxy-β-L-cytosine; m. p. 141–145° C.; $^1$H NMR (DMSO) δ ppm 8.22 and 8.00 (2 br s, 2H, NH$_2$), 7.98 (d, 1H, H-6, J=7.59 Hz), 6.12 (t, 1H, H-1', J=6.5 Hz and J=7.6 Hz), 5.89 (d, 1H, H-5, J=7.59 Hz), 5.3 (br s, 1H, OH-3'), 5.1 (br s, 1H, OH-5'), 4.2 (m, 1H, H-3'), 3.80 (q, 1H, H-4', J=3.6 Hz and J=6.9 Hz), 3.6–3.5 (m, 2H, H-5', H-5"), 2.2–2.0 (m, 2H, H-2', H-2"); FAB<0, (GT) m/e 226 (M–H)$^-$, 110 (B)$^-$; FAB>0 (GT) 228 (M+H)$^+$, 112 (B+2H)$^+$; [α]$_D^{20}$–56.48 (c=1.08 in DMSO); UV (pH 7) λ$_{max}$=270 nm (ε=10000).

Example 25

3',5'-Di-O-benzoyl-2'-deoxy-5-iodo-β-L-uridine (157)

A mixture of compound 155 (105.8 g, 0.242 mol), iodine (76.8 g; Fluka, 99.8%, ref 57650), CAN (66.4 g; cerium ammonium nitrate from Aldrich, >98.5%, ref 21,547-3) and acetonitrile (2550 mL) was stirred at 80° C. for 3 h then the reaction mixture was cooled at room temperature leading to crystallization of compound 157 (86.6 g, 63.5%); m.p. 192–194° C.; $^1$H NMR (DMSO) δ ppm: 8.34 (s, 1H, NH), 8.2–7.2 (m, 11H,2 C$_6$H$_5$CO, H-6), 6.31 (q, 1H, H-1', J=5.5 Hz and J=8.7 Hz), 5.5 (m, 1H, H-3'), 4.7 (m, 2H, H-5', H-5"), 4.5 (m, 1H, H-4'), 2.7 (m, 1H, H-2'), 2.3 (m, 1H, H-2"); FAB<0, (GT) m/e 561 (M–H)$^-$, 237 (B)$^-$; FAB>0 (GT) 563 (M+H)$^+$; [α]$_D^{20}$+39.05 (c=1.05 in DMSO); UV (EtOH 95) υ$_{max}$=281 nm (ε=9000), υ$_{min}$=254 nm (ε=4000), υ$_{max}$=229 nm (ε=31000); Anal. Calcd for C$_{23}$H$_{19}$IN$_2$O$_7$: C, 49.13; H, 3.41; N, 4.98; I, 22.57. Found: C, 49.31; H, 3.53; N, 5.05; I, 22.36.

Example 26

3',5'-Di-O-benzoyl-2'-deoxy-3-N-toluoyl-β-L-thymidine (159)

To a solution of compound 157 (86.6 g, 0.154 mol) in anhydrous pyridine (1530 mL) containing N-ethyldiisopropylamine (53.6 mL; Aldrich, >99.5%, ref 38,764-9) was added, portionwise at 0° C., p-toluoyl chloride (40.6 mL, Aldrich, 98%, ref 10,663-1). The reaction mixture was stirred for 2 h at room temperature, then water was added to stop the reaction and the reaction mixture was extracted with methylene chloride. The organic phase was washed with water, dried over sodium sulfate and evaporated to dryness to give crude 3',5'-di-O-benzoyl-2'-deoxy-3-N-toluoyl-5-iodo-β-L-uridine (158) which can be used for the next step without further purification.

A solution of the crude mixture 158, palladium acetate (3.44 g; Aldrich, >99.98%, ref 37,987-5), triphenylphosphine (8.0 g; Fluka, >97%, ref 93092) in N-methylpyrolidinone (1375 mL; Aldrich, >99%, ref 44,377-8) with triethylamine (4.3 mL) was stirred at room temperature for 45 min. Then, tetramethyltin (42.4 mL; Aldrich, >99%, ref 14,647-1) was added dropwise at 0° C. under argon. After stirring at 100–110° C. overnight, the reaction mixture was poured into water and extracted with diethyl ether. The organic solution was dried over sodium sulfate and concentrated under reduced pressure. The residue was purified by a silica gel column chromatography [eluent: stepwise gradient of ethyl acetate (0–10%) in toluene] to give compound 159 as a foam (42.3 g, 48.3% for the 2 steps). $^1$H NMR (DMSO) δ ppm 8.3–7.2 (m, 15H,2 C$_6$H$_5$CO, 1 CH$_3$C$_6$H$_4$CO, H-6), 6.29 (t, 1H, H-1', J=7.0 Hz), 5.7 (m, 1H, H-3'), 4.7–4.5 (m, 3H, H-5', H-5", H-4'), 2.7–2.6 (m, 2H, H-2', H-2"); FAB<0, (GT) m/e 567 (M–H)$^-$, 449 (M-CH$_3$C$_6$H$_4$CO)$^-$, 243 (B)$^-$, 121 (C$_6$H$_5$COO)$^-$; FAB>0 (GT) 1137 (2M+H)$^+$, 569 (M+H)$^+$, 325 (M–B)$^-$, 245 (B+2H)$^+$, 119 (CH$_3$C$_6$H$_5$CO)$^+$.

Example 27

2'-Deoxy-β-L-thymidine

A solution of compound 159 (42.3 g, 0.074 mol) in methanol saturated with ammonia (1850 mL) was stirred at room temperature for two days. After evaporation of the solvent, the residue was diluted with water and washed several times with ethyl acetate. The aqueous layer was separated, evaporated under reduced pressure and the residue was purified by a silica gel column chromatography [eluent: stepwise gradient of methanol (0–10%) in methylene chloride] to give pure 2'-deoxy-β-L-thymidine (11.62 g, 64.8%) which was crystallized from ethanol; m.p. 185–188° C.; $^1$H NMR (DMSO) δ ppm 11.3 (s, 1H, NH), 7.70 (s, 1H, H-6), 6.2 (pt, 1H, H-1'), 5.24 (d, 1H, OH-3', J=4.2 Hz), 5.08 (t, 1H, OH-5', J=5.1 Hz), 4.2 (m, 1H, H-3'), 3.7 (m, 1H, H-4'), 3.5–3.6 (m, 2H, H-5', H-5"), 2.1–2.0 (m, 2H, H-2', H-2"); FAB<0, (GT) m/e 483 (2M–H)$^-$, 349 (M+T–H)$^-$, 241 (M–H)$^-$, 125 (B)$^-$; FAB>0 (GT) 243 (M+H)$^+$, 127 (B+2H)$^+$;)$^+$; [α]$_D^{20}$ –13.0 (c=1.0 in DMSO); UV (pH 1) υ$_{max}$=267 nm (ε=9700), υ$_{min}$=234 nm (ε=2000).

Example 28

Stereoselective Synthesis of 2'-deoxy-β-L-inosine (β-L-dI)

β-L-dI was synthesized by deamination of 2'-deoxy-β-L-adenosine (β-L-dA) following a procedure previously described in the 9-D-glucopyranosyl series (Ref: I. Iwai, T. Nishimura and B. Shimizu "Synthetic Procedures in Nucleic Acid Chemistry" W. W. Aorbach and R. S. Tipson, eds., John Wiley & Sons, Inc. New York, 1968, 1, 135–138).

Scheme 6:

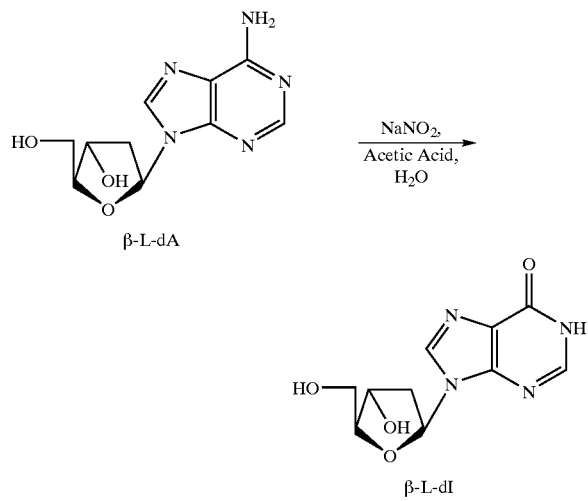

β-L-dA

β-L-dI

Thus, a solution of β-L-dA (200 mg) in a mixture of acetic acid (0.61 mL) and water (19 mL) was heated with sodium nitrite (495 mg), and the mixture was stirred at room temperature overnight. The solution was then evaporated to dryness under diminished pressure. An aqueous solution of the residue was applied to a column of IR-120 (H$^+$) ion-exchange resin, and the column was eluted with water. Appropriate fractions were collected and evaporated to dryness to afford pure β-L-dI which was crystallized from methanol (106 mg, 53% yield not optimized): m.p.= 209°–211° C.; UV (H$_2$O), $\lambda_{max}$=247 nm; $^1$H-NMR (DMSO-d$_6$)=8.32 and 8.07 (2s, 1H each, H-2 and H-8), 6.32 (pt, 1H, H-1'; J=6.7 Hz), 4.4 (m, 1H, H-3'), 3.9 (m, 1H, H-4'), 3.7–3.4 (m, 2H partially obscured by HOD, H-5',5"), 2.6 and 2.3 (2m, 1H each, H-2' and H-2"); mass spectra (mature, glycerol-thioglycerol, 1:1, v/v), FAB>0: 253 (M+H)$^+$, 137 (base+2H)$^+$; FAB<0: 251 (m–H)$^-$, 135 (base); [α]$_D^{20}$=+19.3 (–c 0.88, H$_2$O).

Example 29

Toxicity of Compounds

Toxicity analyses were performed to assess whether any observed antiviral effects are due to a general effect on cell viability. The method used is the measurement of the effect of β-L-dA, β-L-dC and β-L-dT on cell growth in human bone marrow clorogenic assays, as compared to Lamuvidine. The results are provided in Table 1.

TABLE 1

| Compound | CFU-GM (μM) | BFU-E (μM) |
|---|---|---|
| β-L-dA | >10 | >10 |
| β-L-dC | >10 | >10 |
| β-L-dT | >10 | >10 |
| β-L-dU | >10 | >10 |
| Lamuvidine | >10 | >10 |

Example 30

Biological Activity of Phosphorylated Compounds

The ability of the triphosphate derivatives of β-L-dA, β-L-dC, β-L-dU, β-L-2'-dG, β-L-dI, and β-L-dT to inhibit hepatitis B was tested. Table 2 describes the comparative inhibitory activities of triphosphates of β-L-dT (β-L-dT-TP), β-L-dC (β-L-dC-TP), β-L-dU (β-L-dU-TP) and β-L-dA (β-L-dA-TP) on woodchuck hepatitis virus (WHV) DNA polymerase, human DNA polymerases α, β, and γ.

TABLE 2

| Inhibitor | WHV DNA pol IC$_{50}$ | DNA pol α K$_i^b$ (μM) | DNA pol β K$_i^b$ (μM) | DNA pol γ K$_i^b$ (μM) |
|---|---|---|---|---|
| β-L-dT-TP | 0.34 | >100 | >100 | >100 |
| β-L-dA-TP | 2.3 | >100 | >100 | >100 |
| β-L-dC-TP | 2.0 | >100 | >100 | >100 |
| β-L-dU-TP | 8 | >100 | >100 | >100 |

$^a$IC$_{50}$: 50% Inhibitory concentration
$^b$K$_i$ value was determined using calf thymus activated DNA as template-primer and dATP as substrate. Inhibitors were analyzed by Dixon plot analysis. Under these conditions, the calculated mean K$_m$ of human DNA polymerase α for dATP as approximately 2.6 μM. Human DNA polymerase β exhibited a steady state K$_m$ of 3.33 μM for dATP. Human DNA polymerase γ exhibited a steady K$_m$ of 5.2 μM.

Example 31

Antiviral Activity of Compounds

The anti-hepatitis B virus activity of β-L-dA, β-L-dC, β-L-dU, β-L-2'-dG and β-L-dT was tested in transfected Hep G-2 (2.2.15) cells. Table 3 illustrates the effect of β-L-dA, β-L-dC, β-L-dU, and β-L-dT against hepatitis B virus replication in transfected Rep G-2 (2.2.15) cells.

TABLE 3

| Compound | HBV virions$^a$ EC$_{50}$ (μM) | HBV Ri$^b$ EC$_{50}$ (μM) | Cytotoxicity IC$_{50}$ (μM) | Selectivity Index IC$_{50}$/EC$_{50}$ |
|---|---|---|---|---|
| β-L-dT | 0.05 | 0.05 | >200 | >4000 |
| β-L-dC | 0.05 | 0.05 | >200 | >4000 |
| β-L-dA | 0.10 | 0.10 | >200 | >2000 |
| β-L-dI | 1.0 | 1.0 | >200 | >200 |
| β-L-dU | 5.0 | 5.0 | >200 | >40 |

$^a$Extracellular DNA
$^b$Replicative intermediates (Intracellular DNA)

Example 32

Combination Therapy of Compounds

The effect of β-L-dA, β-L-dC and β-L-dT in combination on the growth of hepatitis B was measured in 2.2.15 cells. The results are provided in Table 4.

TABLE 4

| Combination | Ratio | EC$_{50}$ |
|---|---|---|
| L-dC + L-dT | 1:3 | .023 |
| L-dC + L-dT | 1:1 | .053 |
| L-dC + L-dT | 3:1 | .039 |
| L-dC + L-dA | 1:30 | .022 |
| L-dC + L-dA | 1:10 | .041 |
| L-dC + L-dA | 1:3 | .075 |
| L-dT + L-dA | 1:30 | .054 |
| L-dT + L-dA | 1:10 | .077 |
| L-dT + L-dA | 1:3 | .035 |

Each combination produced anti-HBV activity that was synergistic. In addition, the combination of L-dA+L-dC+L-dT was also synergistic in this model.

Example 33

The inhibition of hepatitis B replication in 2.2.15 cells by β-L-dA and β-L-dC, alone and in combination was measured. The results are shown in Table 5.

TABLE 5

| [a]β-L-2'-deoxy-adenosine (μM) | [b]β-L-2'-deoxy-cytidine (μM) | % Inhibition | [c]C.I. |
|---|---|---|---|
| 0.5 | | 90 | |
| 0.05 | | 24 | |
| 0.005 | | 1 | |
| | 0.5 | 95 | |
| | 0.05 | 40 | |
| | 0.005 | 10 | |
| 0.05 | 0.05 | 80 | 0.34 |
| 0.05 | 0.005 | 56 | 0.20 |
| 0.05 | 0.0005 | 50 | 0.56 |
| 0.005 | 0.05 | 72 | 0.35 |
| 0.005 | 0.005 | 54 | 0.35 |
| 0.005 | 0.0005 | 30 | 0.16 |
| 0.0005 | 0.05 | 50 | 0.83 |
| 0.0005 | 0.005 | 15 | 0.28 |
| 0.0005 | 0.0005 | 0 | N.A. |

[a]β-L-2'-deoxy-adenosine: $IC_{50} = 0.09$ μM
[b]β-L-2'-deoxy-cytidine: $IC_{50} = 0.06$ μM
[c]Combination indices values indicate synergism effect (<1), additive effect (=1), and antagonism effect (>1)

Example 35

Efficacy of Compounds

The efficacy of L-dA, L-dT and L-dC against hepadnavirus infection in woodchucks (*Marmota monax*) chronically infected with woodchuck hepatitis virus (WHV) was determined. This animal model of HBV infection is widely accepted and has proven to be useful for the evaluation of antiviral agents directed against HBV.

There were 3 animals per drug group, and 4 animals per control. In group 1, the animals received a vehicle control; group 2 received lamivudine (3TC) (10 mg/kg/day); groups 3–6 received L-dA (0.01, 0.1, 1.0, 10 mg/kg/day, respectively); groups 7–10 received L-dT (0.01, 0.1, 1.0, 10 mg/kg/day, respectively); and groups 11–14 received L-dC (0.01, 0.1, 1.0, 10 mg/kg/day).

Drugs were administered by oral gavage once daily, and blood samples taken on days 0, 1, 3, 7, 14, 21, 28, and on post-treatment days +1, +3, +7, +14, +28 and +56. Assessment of the activity and toxicity was based on the reduction of WHV DNA in serum: dot-blot, quantative PCR.

Figure 5:
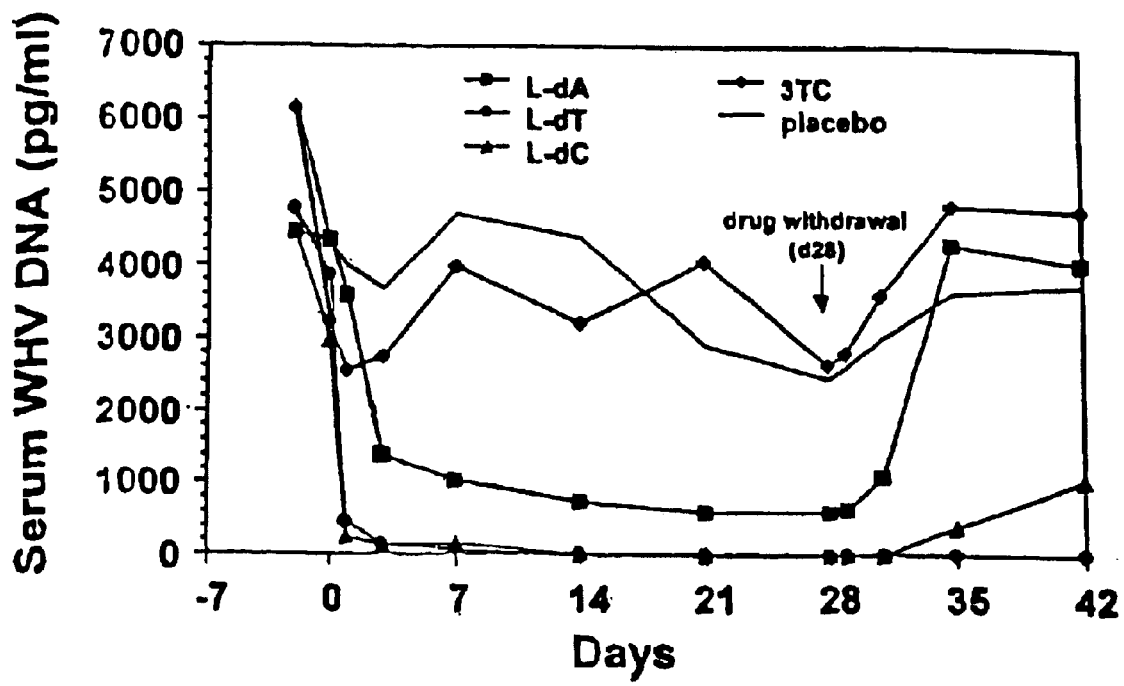
FIG. 5 is a graph that illustrates the antiviral effect of β-L-dA, β-L-dT and β-L-dC in the woodchuck chronic hepatitis model.

The results are illustrated in FIG. 5 and Table 6.

TABLE 6

Antiviral Activity of LdA, LdT, LdC in Woodchuck Model

| day | Control | LdA | LdT | LdC |
|---|---|---|---|---|
| | ng WHV-DNA per ml serum[1,2] | | | |
| 0 | 381 | 436 | 423 | 426 |
| 1 | 398 | 369 | 45 | 123 |
| 3 | 412 | 140 | 14 | 62 |
| 7 | 446 | 102 | 6 | 46 |
| 14 | 392 | 74 | 1 | 20 |

[1]LdA, LdT, LdC administered orally once a day at 10 mg/kg
[2]limit of detection is 1 ng/ml WHV-DNA per ml serum The data show that L-dA, L-dT and L-dC are highly active in this in vivo model. First, viral load is reduced to undetectable (L-dT) or nearly undetectable (L-dA, L-dC) levels. Second, L-dA, L-dT and L-dC are shown to be more active than 3TC (lamivudine) in this model. Third, viral rebound is not detected for at least two weeks after withdrawal of L-dT. Fourth, dose response curves suggest that a modes increase in the dose of L-dA and L-dC would show antiviral activity similar to L-dT. Fifth, all animals receiving the drugs gained weight and no drug-related toxicity was detected.

Example 34

Preparation of Pharmaceutical Compositions

Humans or other hosts infected with hepatitis D can be treated by administering an effective amount of a β-2'-deoxy-β-L-erythro-pentofuranonucleoside, for example, β-L-2'-deoxyadenosine, β-L-2'-deoxycytidine, β-L-2'-deoxyuridine, β-L-2'-deoxyguanosine or β-L-2'-deoxythymidine or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to a patient a therapeutically effective amount of compound to inhibit viral replication in vivo, without causing serious toxic effects in the patient treated. By "inhibitory amount" is meant an amount of active ingredient sufficient to exert an inhibitory effect as measured by, for example, an assay such as the ones described herein.

A preferred dose of the compound for all of the above mentioned conditions will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable prodrug can be calculated based on the weight of the parent nucleoside to be delivered. If the prodrug exhibits activity in itself, the effective dosage can be estimated as above using the weight of the prodrug, or by other means known to those skilled in the art.

The compound is conveniently administered in unit any suitable dosage form, including but not limited to one containing 7 to 3000 mg, preferably 70 to 1400 mg of active ingredient per unit dosage form. A oral dosage of 50–1000 mg is usually convenient.

Ideally the active ingredient should be administered to achieve peak plasma concentrations of the active compound of from about 0.2 to 70 μM, preferably about 1.0 to 10 μM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable derivative or salts thereof can also be mixed with other active materials that do not impair the desired action, or with materials that supplement the desired action, such as antibiotics, antifungals, antiinflammatories, protease inhibitors, or other nucleoside or non-nucleoside antiviral agents. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

This invention has been described with reference to its preferred embodiments. Variations and modifications of the invention, will be obvious to those skilled in the art from the foregoing detailed description of the invention. It is intended that all of these variations and modifications be included within the scope of the this invention.

We claim:

1. A method for treating a host infected with hepatitis D virus comprising administering an effective hepatitis D treatment amount of a biologically active 2'-deoxy-β-L-erythro-pentofuranonucleoside or a pharmaceutically acceptable salt thereof in combination or alternation with interferon to a host in need thereof.

2. A method for treating a host infected with hepatitis D virus comprising administering an effective hepatitis D treatment amount of 2'-deoxy-β-L-erythro-pentofuranonucleoside of the formula:

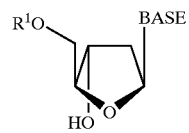

or a pharmaceutically acceptable salt thereof, wherein $R^1$ is selected from the group consisting of H, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and BASE is a purine or pyrimidine base that may optionally be substituted;

in combination or alternation with interferon to a host in need thereof.

3. The method of claim 2, wherein the 2'-deoxy-β-L-erythro-pentofuranonucleoside is a β-L-2'-deoxypurine of the formula:

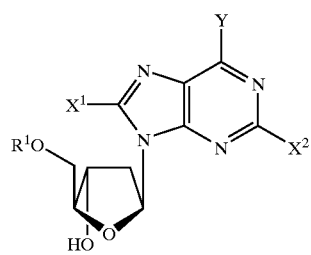

or a pharmaceutically acceptable salt thereof, wherein $R^1$ is selected from the group consisting of H, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

Y is $OR^3$, $NR^3R^4$ or $SR^3$; and $X^1$ and $X^2$ are independently selected from the group consisting of H, straight chained, branched or cyclic alkyl, CO-alkyl, CO-aryl, CO-alkoxyalkyl, halogen, $OR^5$, $NR^5NR^6$ or $SR^5$; and $R^3$, $R^4$, $R^5$ and $R^6$ are independently H, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

4. The method of claim 3, wherein the 2'-deoxy-β-L-erythro-pentofuranonucleoside is a β-L-2'-deoxyadenosine of the formula:

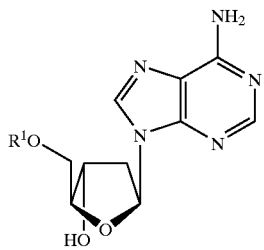

or pharmaceutically acceptable salt thereof, wherein $R^1$ is H, mono, di or triphosphate, acyl, alkyl, or a stabilized phosphate derivative.

5. The method of claim 4, wherein $R^1$ is hydrogen.

6. The method of claim 5, wherein $R^1$ is acyl.

7. The method of claim 6, wherein the acyl is derived from an amino acid.

8. The method of claim 7, wherein the amino acid is valine.

9. The method of claim 3, wherein the 2'-deoxy-β-L-erythro-pentofuranonucleoside is a β-L-2'-deoxyguanosine of the formula:

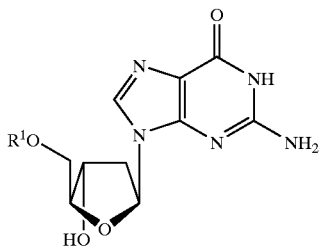

or pharmaceutically acceptable salt thereof, wherein $R^1$ is H, mono, di or triphosphate, acyl, alkyl, or a stabilized phosphate derivative.

10. The method of claim 3, wherein the 2'-deoxy-β-L-erythro-pentofuranonucleoside is a β-L-2'-deoxyinosine of the formula:

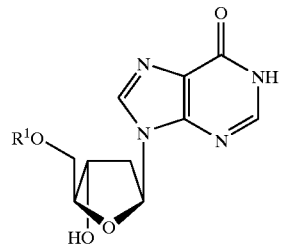

or pharmaceutically acceptable salt thereof, wherein $R^1$ is H, mono, di or triphosphate, acyl, alkyl, or a stabilized phosphate derivative.

11. The method of claim 2, wherein the 2'-deoxy-β-L-erythro-pentofuranonucleoside is a β-L-2'-deoxypyrimidine of the formula:

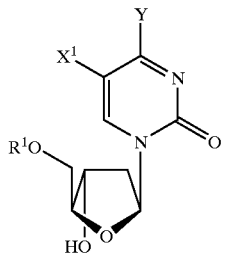

or a pharmaceutically acceptable salt or prodrug thereof, wherein $R^1$ is selected from the group consisting of H, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

Y is $OR^3$, $NR^3R^4$ or $SR^3$; and $X^1$ is selected from the group consisting of H, straight chained, branched or cyclic alkyl, CO-alkyl, CO-aryl, CO-alkoxyalkyl, halogen, $OR^5$, $NR^5NR^6$ or $SR^5$; and $R^3$, $R^4$, $R^5$ and $R^6$ are independently H, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

12. The method of claim 11, wherein the 2'-deoxy-β-L-erythro-pentofuranonucleoside is a β-L-2'-deoxyuridine of the formula:

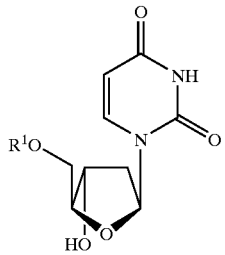

or pharmaceutically acceptable salt thereof, wherein $R^1$ is H, mono, di or triphosphate, acyl, alkyl, or a stabilized phosphate derivative.

13. A method for treating a host infected with hepatitis D virus comprising administering an effective hepatitis D treatment amount of a β-L-2'-deoxycytidine of the formula:

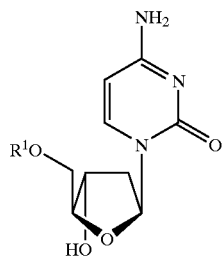

or pharmaceutically acceptable salt thereof, wherein $R^1$ is H, mono, di or triphosphate, acyl, alkyl, or a stabilized phosphate derivative;

in combination or alternation with interferon to a host in need thereof.

14. The method of claim 13, wherein $R^1$ is hydrogen.
15. The method of claim 14, wherein $R^1$ is acyl.
16. The method of claim 15, wherein the acyl is derived from an amino acid.
17. The method of claim 16, wherein the amino acid is valine.
18. A method for treating a host infected with hepatitis D virus comprising administering an effective hepatitis D treatment amount of a β-L-thymidine of the formula:

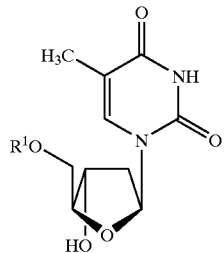

or pharmaceutically acceptable salt thereof, wherein $R^1$ is H, mono, di or triphosphate, acyl, alkyl or a stabilized phosphate derivative;

in combination or alternation with interferon to a host in need thereof.

19. The method of claim 18, wherein $R^1$ is hydrogen.
20. The method of claim 19, wherein $R^1$ is acyl.
21. The method of claim 20, wherein the acyl is derived from an amino acid.
22. The method of claim 21, wherein the amino acid is valine.
23. A method for treating a host infected with hepatitis D virus comprising administering an effective hepatitis D treatment amount of a β-L-2'-deoxycytidine of the formula:

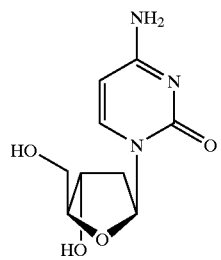

or pharmaceutically acceptable salt thereof, in combination or alternation with interferon.

24. A method for treating a host infected with hepatitis D virus comprising administering an effective hepatitis D treatment amount of a β-L-thymidine of the formula:

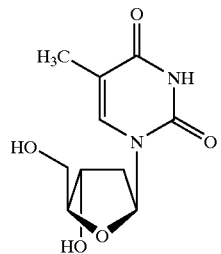

or pharmaceutically acceptable salt thereof, in combination or alternation with interferon.

25. The method of any one of claims 1–24, wherein the host is a human.

* * * * *